(12) United States Patent
Kawase et al.

(10) Patent No.: US 7,582,197 B2
(45) Date of Patent: Sep. 1, 2009

(54) GAS CONCENTRATION MEASURING APPARATUS WITH FAILURE MONITOR

(75) Inventors: Tomoo Kawase, Aichi-ken (JP); Eiichi Kurokawa, Okazaki (JP)

(73) Assignee: DENSO Corporation, Kariya (JP)

( * ) Notice: Subject to any disclaimer, the term of this patent is extended or adjusted under 35 U.S.C. 154(b) by 777 days.

(21) Appl. No.: 11/091,916

(22) Filed: Mar. 29, 2005

(65) Prior Publication Data
US 2005/0217347 A1    Oct. 6, 2005

(30) Foreign Application Priority Data
Apr. 1, 2004   (JP) ............... 2004-108992
May 19, 2004   (JP) ............... 2004-148622

(51) Int. Cl.
*G01N 27/26*   (2006.01)

(52) U.S. Cl. ............ 204/401; 204/426; 204/229.8; 73/23.31; 73/23.32

(58) Field of Classification Search ............ 204/401, 204/426, 229.8; 73/23.31, 23.32
See application file for complete search history.

(56) References Cited

U.S. PATENT DOCUMENTS 4,777,922 A   10/1988   Mieno
5,709,198 A   1/1998    Sagisaka et al.
6,009,866 A   1/2000    Sagasaka et al.
6,120,663 A * 9/2000    Kato et al. .......... 204/401
6,136,169 A * 10/2000   Okamoto ............ 204/401
6,314,790 B1  11/2001   Sagisaka et al.

FOREIGN PATENT DOCUMENTS

| JP | 62-225945 A | 10/1987 |
| JP | 8-271475    | 10/1996 |
| JP | 9-4494      | 1/1997  |

OTHER PUBLICATIONS

Office Action and English translation thereof, in counterpart application JP 2004-148622, mailed Sep. 4, 2007.

* cited by examiner

*Primary Examiner*—Alex Noguerola
*Assistant Examiner*—J. Christopher Ball
(74) *Attorney, Agent, or Firm*—Nixon & Vanderhye P.C.

(57) ABSTRACT

A gas concentration measuring apparatus for use in air-fuel ratio control of motor vehicle engines is provided which is designed to detect and identify a cause of failure in operation of an A/F sensor. The apparatus works to apply the voltage to a sensor element and sweep it to produce a change in electrical current flowing through the sensor element for measuring the impedance of the sensor element. The apparatus samples values of the change in the current, a sensor output indicating an air-fuel ratio of mixture supplied to the engine, etc., before and/or after the sensor element is activated and uses a combination thereof to identify the cause of the failure of the A/F sensor.

19 Claims, 19 Drawing Sheets

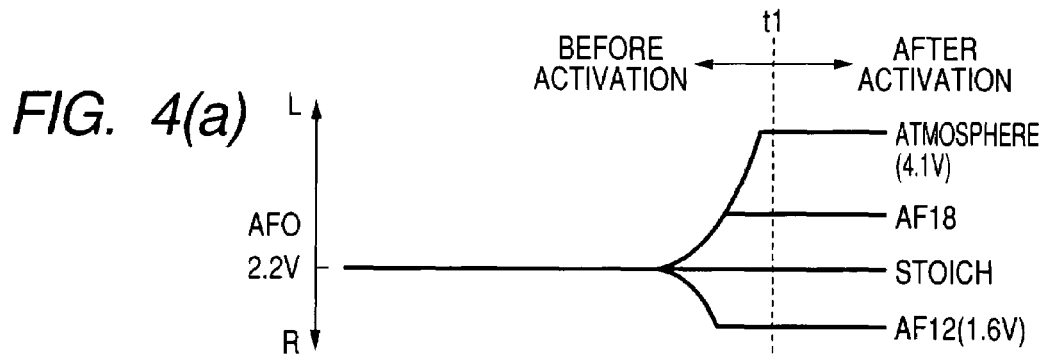
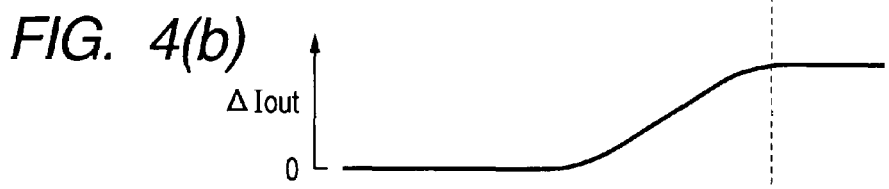
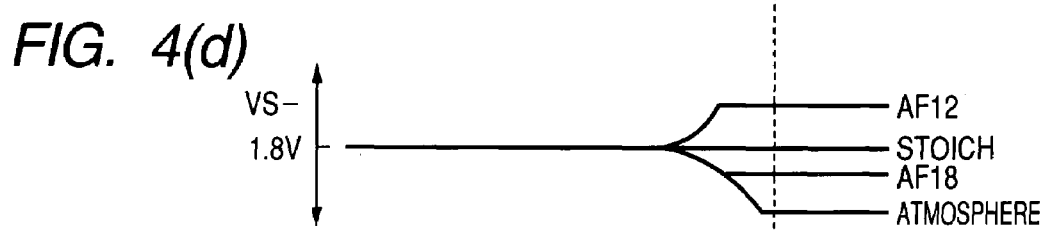
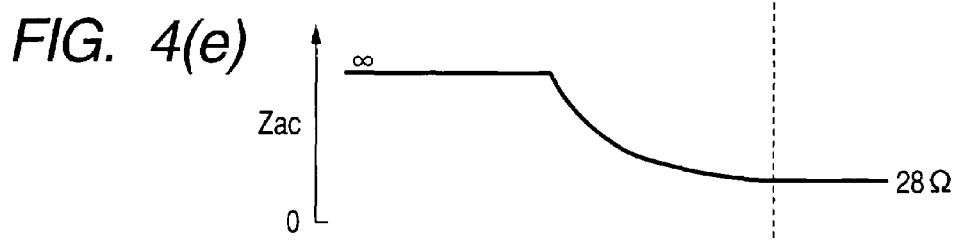

FIG. 5

| | BEFORE ACTIVATION | | | | AFTER ACTIVATION | | | |
|---|---|---|---|---|---|---|---|---|
| | ΔIout | AFO | VS+ | VS− | ΔIout | AFO | VS+ | VS− |
| SENSOR WIRE BREAKAGE | 0V(○) | 2.2V(○) | 2.2V(○) | 1.8V(○) | 0V(×) | 2.2V(○) | 2.2V(○) | 1.8V(○) |
| VB SHORT OF T1 | 0V(○) | 5.0V(×) | 5.0V(×) | 1.8V(○) | 0V(×) | 5.0V(×) | 5.0V(×) | 5.0V(×) |
| GND SHORT OF T1 | 0V(○) | 5.0V(×) | 0V(×) | 1.8V(○) | 0V(×) | 5.0V(×) | 0V(×) | 0.9V(×) |
| VB SHORT OF T2 | 0V(○) | 2.2V(○) | 2.2V(○) | 5.0V(×) | 0V(×) | 5.0V(×) | 5.0V(×) | 5.0V(×) |
| GND SHORT OF T2 | 0V(○) | 2.2V(○) | 2.2V(○) | 0V(×) | 0V(×) | 5.0V(×) | 2.2V(○) | 0V(×) |
| T1-T2 SHORT | 0V(○) | 5.0V(×) | 1.1V(×) | 1.1V(×) | 0V(×) | 5.0V(×) | 1.1V(×) | 1.1V(×) |
| NORMAL | 0V | 2.2V | 2.2V | 1.8V | 2.9V(28Ω) | 1.6~4.1V | 2.2V | 1.4~2.0V |

FIG. 6

| | BEFORE ACTIVATION | | AFTER ACTIVATION | |
|---|---|---|---|---|
| | Δ Iout | AFO | Δ Iout | AFO |
| SENSOR WIRE BREAKAGE | 0V(O) | 2.2V(O) | 0V(×) | 2.2V(O) |
| VB/GND SHORT OF T1 & T1−T2 SHORT | 0V(O) | 5.0V(×) | 0V(×) | 5.0V(×) |
| VB/GND SHORT OF T2 | 0V(O) | 2.2V(O) | 0V(×) | 5.0V(×) |
| NORMAL | 0V | 2.2V | 2.9V(28Ω) | 1.6~4.1V |

FIG. 8

| | BEFORE ACTIVATION | | | AFTER ACTIVATION | | |
|---|---|---|---|---|---|---|
| | ΔIout | AFO | VS+ | ΔIout | AFO | VS+ |
| SENSOR WIRE BREAKAGE | 0V(○) | 2.2V(○) | 2.2V(○) | 0V(×) | 2.2V(○) | 2.2V(○) |
| VB SHORT OF T1 | 0V(○) | 5.0V(×) | 5.0V(○) | 0V(×) | 5.0V(×) | 5.0V(×) |
| GND SHORT OF T1 | 0V(○) | 5.0V(×) | 0V(×) | 0V(×) | 5.0V(×) | 0V(×) |
| VB SHORT OF T2 | 0V(○) | 2.2V(○) | 2.2V(○) | 0V(×) | 5.0V(×) | 5.0V(×) |
| GND SHORT OF T2 | 0V(○) | 2.2V(○) | 2.2V(○) | 0V(×) | 5.0V(×) | 2.2V(○) |
| T1-T2 SHORT | 0V(○) | 5.0V(×) | 1.1V(×) | 0V(×) | 5.0V(×) | 1.1V(×) |
| NORMAL | 0V | 2.2V | 2.2V | 2.9V(28Ω) | 1.6~4.1V | 2.2V |

FIG. 10

|  | BEFORE ACTIVATION | | AFTER ACTIVATION | |
| --- | --- | --- | --- | --- |
|  | Δ Iout | VS− | Δ Iout | VS− |
| SENSOR WIRE BREAKAGE | 0V(○) | 1.8V(○) | 0V(×) | 1.8V(○) |
| VB SHORT OF T1 | 0V(○) | 1.8V(○) | 0V(×) | 5.0V(×) |
| GND SHORT OF T1 | 0V(○) | 1.8V(○) | 0V(×) | 0.9V(×) |
| VB SHORT OF T2 | 0V(○) | 5.0V(×) | 0V(×) | 5.0V(×) |
| GND SHORT OF T2 | 0V(○) | 0V(×) | 0V(×) | 0V(×) |
| T1−T2 SHORT | 0V(○) | 1.1V(×) | 0V(×) | 1.1V(×) |
| NORMAL | 0V | 1.8V | 2.9V(28Ω) | 1.4～2.0V |

FIG. 13

|  | BEFORE ACTIVATION ||||  AFTER ACTIVATION ||||
|  | ΔIout | AFO | VS+ | VS− | ΔIout | AFO | VS+ | VS− |
|---|---|---|---|---|---|---|---|---|
| SENSOR WIRE BREAKAGE | 0V(○) | 2.2V(○) | 2.6V(○) | 2.2V(○) | 0V(×) | 2.2V(○) | 2.6V(○) | 2.2V(○) |
| VB SHORT OF T1 | 0V(○) | 2.2V(○) | 5.0V(×) | 2.2V(○) | 0V(×) | 0V(×) | 5.0V(×) | 5.0V(×) |
| GND SHORT OF T1 | 0V(○) | 2.2V(○) | 0V(×) | 2.2V(○) | 0V(×) | 0V(×) | 0V(×) | 2.2V(○) |
| VB SHORT OF T2 | 0V(○) | 0V(×) | 2.6V(○) | 5.0V(×) | 0V(×) | 0V(×) | 5.0V(×) | 5.0V(×) |
| GND SHORT OF T2 | 0V(○) | 0V(×) | 2.6V(○) | 0V(×) | 0V(×) | 0V(×) | 3.5V(×) | 0V(×) |
| T1–T2 SHORT | 0V(○) | 5.0V(×) | 3.3V(×) | 3.3V(×) | 0V(×) | 5.0V(×) | 3.3V(×) | 3.3V(×) |
| NORMAL | 0V | 2.2V | 2.6V | 2.2V | 2.9V(28Ω) | EQUIVALENT TO A/F | 2.4~3.0V | 2.2V |

FIG. 17

|  | BEFORE ACTIVATION | | | AFTER ACTIVATION | | |
|---|---|---|---|---|---|---|
|  | Vz | AFO | Vip | Vz | AFO | Vip |
| UN BREAKAGE | 0V(○) | 2.5V(○) | 2.0V(○) | 0V(×) | 0V(×) | 2.4V(○) |
| UN/VB | 5.0V(×) | 2.5V(○) | 0V(×) | 2.5V(○) | 2.5V(○) | 0V(×) |
| UN/GND | 5.0V(×) | 2.5V(○) | 5.0V(×) | 2.5V(○) | 2.5V(○) | 5.0V(×) |
| UN/VM | 5.0V(×) | 2.5V(○) | 2.5V(×) | 2.5V(○) | 2.5V(○) | 2.5V(×) |
| VM BREAKAGE | 0V(○) | 2.5V(○) | 2.0V(○) | 2.24V(○) | 2.5V(○) | 3.0V(×) |
| VM/VB | 0V(○) | 2.5V(○) | 2.0V(○) | 2.24V(○) | 0V(×) | 5.0V(×) |
| VM/GND | 0V(○) | 2.5V(○) | 2.0V(○) | 2.24V(○) | 5.0V(×) | 5.0V(×) |
| VM/IP | 0V(○) | 1.25~4.57V(○) | 2.5V(×) | 2.24V(○) | 5.0V(×) | 3.0V(×) |
| IP BREAKAGE | 0V(○) | 2.5V(○) | 2.0V(○) | 2.24V(○) | 2.5V(○) | 5.0V(×) |
| IP/VB | 0V(○) | 0V(×) | 5.0V(×) | 2.24V(○) | 0V(×) | 5.0V(×) |
| IP/GND | 0V(○) | 5.0V(×) | 0V(×) | 2.24V(○) | 5.0V(×) | 5.0V(×) |
| IP/UN | 5.0V(×) | 2.5V(○) | 3.0V(×) | 2.34V(○) | 2.5V(○) | 0V(×) |
| NORMAL | 0V | 2.5V | 2.0V | 2.24V | 1.6~4.1V | 1.98~3.48V |

GAS CONCENTRATION MEASURING APPARATUS WITH FAILURE MONITOR

CROSS REFERENCE TO RELATED DOCUMENT

The present application claims the benefit of Japanese Patent Application No. 2004-108992 filed on Apr. 1, 2004 and Japanese Paten Application No. 2004-148622 filed on May 19, 2004, disclosures of which are incorporated herein by reference.

BACKGROUND OF THE INVENTION

1. Technical Field of the Invention

The present invention relates generally to a gas concentration measuring apparatus which may be used in measuring the concentration of a preselected component of exhaust emissions of automotive engines, and more particularly to such a gas concentration measuring apparatus equipped with a failure monitor designed to detect a failure in operation of a gas sensor such as a wire disconnection, a power supply short, or a ground short.

2. Background Art

Limiting current air-fuel (A/F) ratio sensors (also called lambda sensors) are known which measure the concentration of oxygen ($O_2$) contained in exhaust emissions of motor vehicle engines as indicating an air-fuel ratio of a mixture supplied to the engine. A typical one of the A/F sensors includes a sensor element made up of a solid electrolyte body and a pair of electrodes affixed to the solid electrolyte body. The measurement of concentration of oxygen is achieved by applying the voltage to the solid electrolyte body through the electrodes to produce a flow of electrical current through the sensor element as a function of the concentration of oxygen and sampling the electrical current to determine the A/F ratio.

Usually, if terminals connecting with ends of the sensor element are disconnected, short-circuited to a power supply, ground, or each other, it will result in a failure in measuring the current flowing through the sensor element accurately, which leads to an error in determining the concentration of oxygen contained in the exhaust emissions of the engine (i.e. the A/F ratio of a mixture supplied to the engine). In order to avoid this problem, conventional systems are designed to sample and take voltages appearing at the terminals of the sensor element into a CPU through A/D converters and determine that the A/F sensor is malfunctioning when outputs of the A/D converters are shifted out of a normal voltage range. This structure requires as many additional A/D converters as the terminals of the sensor element, thus resulting in increased complexity of the structure. Improvement of such a structure is, therefore, being sought.

Japanese Patent No. 3446400, assigned to the same assignee as that of this application, teaches a failure diagnosis system for A/F sensors used in air-fuel ratio control of automotive engines which is designed to monitor the degree of activation of the A/F sensor to determine whether the A/F sensor is malfunctioning or not. The failure diagnosis system also works to determine that the A/F sensor is malfunctioning if the A/F sensor is determined not to be activated yet after once being determined to have been activated after start-up of the engine. Many other failure diagnosis systems for A/F sensors have been proposed in recent years, but however, emission regulations have been increasingly tightened. The failure diagnosis systems are, therefore, being required to detect the failure of the A/F sensor with high accuracy and/or identify the cause thereof.

SUMMARY OF THE INVENTION

It is therefore a principal object of the invention to avoid the disadvantages of the prior art.

It is another object of the invention to provide a simplified structure of a gas concentration measuring apparatus designed to detect a failure in operation of an gas concentration sensor and/or identify the cause of such a failure.

According to one aspect of the invention, there is provided a gas concentration measuring apparatus which may be employed in determining an air-fuel ratio of an automotive engine for use in air-fuel ratio control. The gas concentration measuring apparatus comprises: (a) a gas concentration sensor equipped with a sensor element which is made of a solid electrolyte body and a pair of electrodes affixed to the solid electrolyte body; (b) a sensor control circuit connected to the electrodes of the sensor element through a positive and a negative terminal, when a gas concentration measuring mode is entered, the sensor control circuit applying a voltage across the electrodes of the sensor element to produce a flow of electrical current through the sensor element and sampling the electrical current through a current-measuring resistor to output a sensor current signal as indicating a concentration of a gas to be measured, when an internal resistance measuring mode is entered, the sensor control circuit working to perform one of a voltage sweep mode and a current sweep mode, in the voltage sweep mode, the sensor control circuit applying a voltage to the sensor element and sweeping the applied voltage in an ac form to sample a resulting change in voltage provided by the sensor element, in the current sweep mode, the sensor control circuit supplying a current to the sensor element and sweeping the supplied current in an ac form to sample a resulting change in current provided by the sensor element, the sensor control circuit outputting one of the resulting changes in voltage and current as an internal resistance signal; and (c) a failure monitor working to sample values of the sensor current signal before and after the sensor element is activated and a value of the internal resistance signal after the sensor element is activated. The failure monitor detects a failure in the gas concentration sensor based on the sampled values.

Typical causes of failure which would arise in a gas concentration sensor of the type, as described above, are a disconnection between the sensor element and a circuit line and an electrical short of the sensor element to a power supply or ground. Combinations of values of current (i.e., the sensor current signal) flowing through the sensor element before and after the sensor element is activated and a value of the internal resistance signal after the sensor element is activated usually depend upon the causes of failure in the gas concentration sensor. The presence of failure in the gas concentration sensor may, therefore, be detected by monitoring a combination of the sensor current signal and the internal resistance signal. In other words, the failure of the gas concentration sensor may be detected using two failure-detecting parameters. Accordingly, in a case where the failure monitor is implemented by a microcomputer, it may be designed to have only two A/D converters to which the failure-detecting parameters are inputted, thus permitting the microcomputer and a circuit arrangement connected to the microcomputer to be simplified in structure.

In the preferred mode of the invention, the failure monitor determines whether the gas concentration sensor is failing or not based on the value of the internal resistance signal, as sampled after the gas concentration sensor is activated and also identifies a cause of failure of the gas concentration sensor based on the values of the sensor current signals, as sampled before and after the gas concentration sensor is activated.

The current-measuring resistor is connected to one of the positive and negative terminals. When the gas concentration measuring mode is entered, the failure monitor may sample, instead of the value of the sensor current signal, a voltage appearing at an end of the current-measuring resistor which changes as a function of the current flowing through the sensor element. When the internal resistance measuring mode is entered, the failure monitor may sample, as the value of the internal resistance signal, a voltage appearing at the end of the current-measuring resistor which changes as a function of an internal resistance of the sensor element.

The failure monitor may also sample at least one of voltages appearing at the positive and negative terminals one of before and after the sensor element is activated. The failure monitor detects the failure of the gas concentration sensor based on the sampled one of the voltages in addition to the values of the sensor current signal, as sampled before and after the sensor element is activated and the value of the internal resistance signal, as sampled after the sensor element is activated.

The failure monitor may monitor whether the sampled one of the voltages developed at the positive and negative terminals is held at an upper or a lower limit of an input signal voltage range of the sensor control circuit to identify whether the gas concentration sensor is short-circuited to a power supply or ground.

The failure monitor may store therein a table listing unusual values shown by the sensor current signal and the internal resistance signal when the gas concentration sensor is failing in operation and looks up a combination of the sampled values from the table to identify the cause of the failure of the gas concentration sensor.

The failure monitor may sample the values of the sensor current signal and the internal resistance signal at times other than during transition of activation of the sensor element. This ensures the stability in detecting the failure of the gas concentration sensor.

According to the second aspect of the invention, there is provided a gas concentration measuring apparatus which comprises: (a) a gas concentration sensor equipped with a sensor element which is made of a solid electrolyte body and a pair of electrodes affixed to the solid electrolyte body; (b) a sensor control circuit connected to the electrodes of the sensor element through a positive and a negative terminal, when a gas concentration measuring mode is entered, the sensor control circuit applying a voltage across the electrodes of the sensor element to produce a flow of electrical current through the sensor element and sampling the electrical current through a current-measuring resistor connected to one of the positive and negative terminals to output a sensor current signal as indicating a concentration of a gas to be measured, when an internal resistance measuring mode is entered, the sensor control circuit working to perform one of a voltage sweep mode and a current sweep mode, in the voltage sweep mode, the sensor control circuit applying a voltage to the sensor element and sweeping the applied voltage in an ac form to sample a resulting change in voltage provided by the sensor element, in the current sweep mode, the sensor control circuit supplying a current to the sensor element and sweeping the supplied current in an ac form to sample a resulting change in current provided by the sensor element, the sensor control circuit outputting one of the resulting changes in voltage and current as an internal resistance signal; and (c) a failure monitor working to sample values of voltages appearing at the other of the positive and negative terminals before and after the sensor element is activated and a value of the internal resistance signal after the sensor element is activated. The failure monitor detects a failure in the gas concentration sensor based on the sampled values.

In the preferred mode of the invention, the failure monitor may determine whether the gas concentration sensor is failing or not based on the value of the internal resistance signal, as sampled after the gas concentration sensor is activated and also identify a cause of failure of the gas concentration sensor based on the values of the voltages, as sampled before and after the gas concentration sensor is activated.

The failure monitor may store therein a table listing unusual values shown by the internal resistance signal and the voltages when the gas concentration sensor is failing in operation and look up a combination of the sampled values from the table to identify a cause of the failure of the gas concentration sensor.

The failure monitor may sample the values of the internal resistance signal and the voltages at times other than during transition of activation of the sensor element.

According to the third aspect of the invention, there is provided a gas concentration measuring apparatus which comprises: (a) a gas concentration sensor equipped with a sensor element which includes a first cell and a second cell, the first cell being made of a solid electrolyte material and working to perform an oxygen pumping operation to produce an electrical current as a function of a pumped amount of oxygen, the second cell being made of a solid electrolyte material and working to produce an electromotive force as a function of a concentration of oxygen contained in a gas to be measured; (b) a sensor control circuit working to perform a gas concentration measuring mode and an internal resistance measuring mode, when the gas concentration measuring mode is entered, the sensor control circuit applying a voltage to the first cell, controlling the applied voltage as a function of the electromotive force produced by the second cell to produce a flow of an electrical current through the first cell, and sampling the electrical current through a current-measuring resistor to output the sampled electrical current as a sensor current signal as indicating a concentration of a gas to be measured, when the internal resistance measuring mode is entered, the sensor control circuit working to perform one of a voltage sweep mode and a current sweep mode, in the voltage sweep mode, the sensor control circuit applying a voltage to the second cell and sweeping the applied voltage in an ac form to sample a resulting change in voltage provided by the second cell, in the current sweep mode, the sensor control circuit supplying a current to the second cell and sweeping the supplied current in an ac form to sample a resulting change in current provided by the second cell, the sensor control circuit outputting one of the resulting changes in voltage and current as an internal resistance signal; and (c) a failure monitor working to sample values of the sensor current signal, the internal resistance signal, and voltages appearing at least one of positive and negative terminals connected to the first cell before and after the sensor element is activated. The failure monitor detects a failure in the gas concentration sensor based on the sampled values.

In the preferred mode of the invention, the failure monitor may work to discriminate among a disconnection, a short to a power supply, a short to ground, and a terminal-to-terminal short of each of the positive and negative terminals connected to the first cell and positive and negative terminal connected to the second cell.

The second cell is connected to a positive and a negative terminal one of which is a common terminal shared with one of the positive and negative terminals connected to the first cell. The common terminal is applied with a reference voltage. The failure monitor samples voltages appearing at one of the positive and negative terminals connected to the first cell that is not the common terminal before and after the sensor element is activated.

The failure monitor may store therein a table listing unusual values shown by the internal resistance signal, the sensor current signal, the internal resistance signal, and the voltages appearing at the one of the positive and negative terminals connected to the first cell when the gas concentration sensor is failing in operation. The failure monitor looks up a combination of the sampled values from the table to identify the cause of the failure of the gas concentration sensor.

The failure monitor may sample the values of the sensor current signal, the internal resistance signal, and the voltages appearing at the one of the positive and negative terminals connected to the first cell at times other than during transition of activation of the sensor element before and after the sensor element is activated.

According to the fourth aspect of the invention, there is provided a gas concentration measuring apparatus which comprises: (a) a gas concentration sensor equipped with a sensor element which is made of a solid electrolyte body and a pair of electrodes affixed to the solid electrolyte body; (b) a sensor control circuit connected to the electrodes of the sensor element through a positive and a negative terminal, when a gas concentration measuring mode is entered, the sensor control circuit applying a voltage across the electrodes of the sensor element within a given applied-voltage control range to produce a flow of electrical current through the sensor element and sampling the electrical current to output a sensor current signal as indicating a concentration of a gas to be measured, the sensor control circuit also sampling voltages appearing at the positive and negative terminals; and (c) a failure monitor working to monitor a failure in the gas concentration sensor. When the voltages at the position and negative terminals, as sampled by the sensor control circuit, are identical with each other, one of the voltages at the positive and negative terminals lies within the applied-voltage control range, and the sensor current signal has an unusual value, the failure monitor determines that an electrical short has occurred between the positive and negative terminals.

In the preferred mode of the invention, when the one of the voltages at the positive and negative terminals is less than a given threshold level, the failure monitor determines that the one of the voltages lies within the applied-voltage control range.

According to the fifth aspect of the invention, there is provided a gas concentration measuring apparatus which comprises: (a) a gas concentration sensor equipped with a sensor element which is made of a solid electrolyte body and a pair of electrodes affixed to the solid electrolyte body; (b) a sensor control circuit connected to the electrodes of the sensor element through a positive and a negative terminal, when a gas concentration measuring mode is entered, the sensor control circuit applying a voltage across the electrodes of the sensor element within a given applied-voltage control range to produce a flow of electrical current through the sensor element and sampling the electrical current to output a sensor current signal as indicating a concentration of a gas to be measured, the sensor control circuit also sampling voltages appearing at the positive and negative terminals; and (c) a failure monitor working to monitor a failure in the gas concentration sensor. When the voltages at the position and negative terminals, as sampled by the sensor control circuit before the sensor element is activated, are identical with each other, and the sensor current signal has an unusual value, the failure monitor determines that an electrical short has occurred between the positive and negative terminals.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIGS. 4(*a*), 4(*b*), 4(*c*), 4(*d*), 4(*e*), and 4(*f*) are time charts which demonstrate variations in an A/F output voltage AFO, a change ΔIout in an impedance current signal, voltages VS+ and VS− appearing at terminals leading to a sensor element, an impedance Zac of the sensor element, and temperature of the sensor element before and after the sensor element is activated;

FIG. 5 is a table which demonstrate combinations of selected failure-detecting parameters before and after a sensor element is activated in events of different types of causes of failure in an A/F sensor;

FIG. 6 is a table which demonstrate combinations of selected failure-detecting parameters before and after a sensor element is activated in events of different types of causes of failure in an A/F sensor;

FIG. 8 is a table which demonstrate combinations of selected failure-detecting parameters before and after a sensor element is activated in events of different types of causes of failure in an A/F sensor for use in a gas concentration measuring apparatus of the second embodiment of the invention;

FIG. 10 is a table which demonstrate combinations of selected failure-detecting parameters before and after a sensor element is activated in events of a plurality of different types of causes of failure in an A/F sensor for use in a gas concentration measuring apparatus of the third embodiment of the invention;

FIG. 13 is a table which demonstrate combinations of selected failure-detecting parameters before and after a sensor element is activated in events of a plurality of different types of causes of failure in an A/F sensor for use in a gas concentration measuring apparatus of the fourth embodiment of the invention;

FIG. 17 is a table which demonstrate combinations of selected failure-detecting parameters before and after a sensor element is activated in events of a plurality of different types of causes of failure in an A/F sensor for use in a gas concentration measuring apparatus of the fifth embodiment of the invention;

DESCRIPTION OF THE PREFERRED EMBODIMENTS

Figure 1:
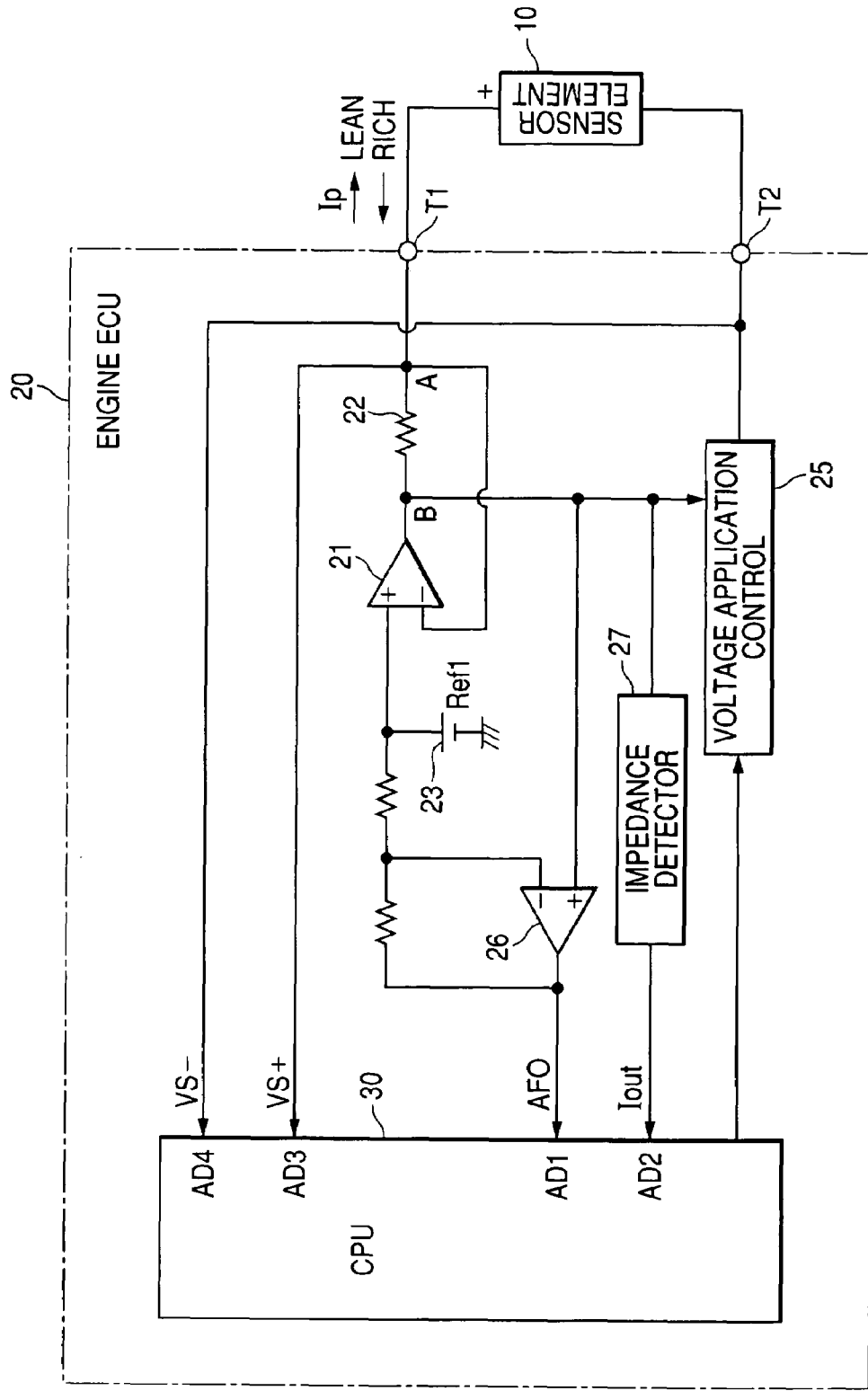
FIG. 1 is a circuit diagram which shows an electric structure of a gas concentration measuring apparatus according to the first embodiment of the invention.

Referring to the drawings, wherein like reference numbers refer to like parts in several views, particularly to FIG. 1, there is shown a gas concentration measuring apparatus designed to measure the concentration of oxygen ($O_2$) contained in exhaust emissions of an automotive engine as indicating an air-fuel ratio of a mixture supplied to the engine. The measured concentration is used in an air-fuel ratio control system implemented by an engine ECU. The air-fuel ratio control system works to perform a stoichiometric burning control to bring the air-fuel ratio near the stoichiometric air-fuel ratio under feedback control and a lean-burn control to bring the air-fuel ratio to within a given lean range under feedback control.

The gas concentration measuring apparatus includes a microcomputer 20 implemented by an engine ECU, a sensor control circuit 30 implemented by a CPU, and an oxygen sensor (will be referred to as an air-fuel (A/F) sensor below) which works to produce a current signal as a function of concentration of oxygen contained in exhaust emissions introduced into a gas chamber formed in the A/F sensor.

Figure 2:
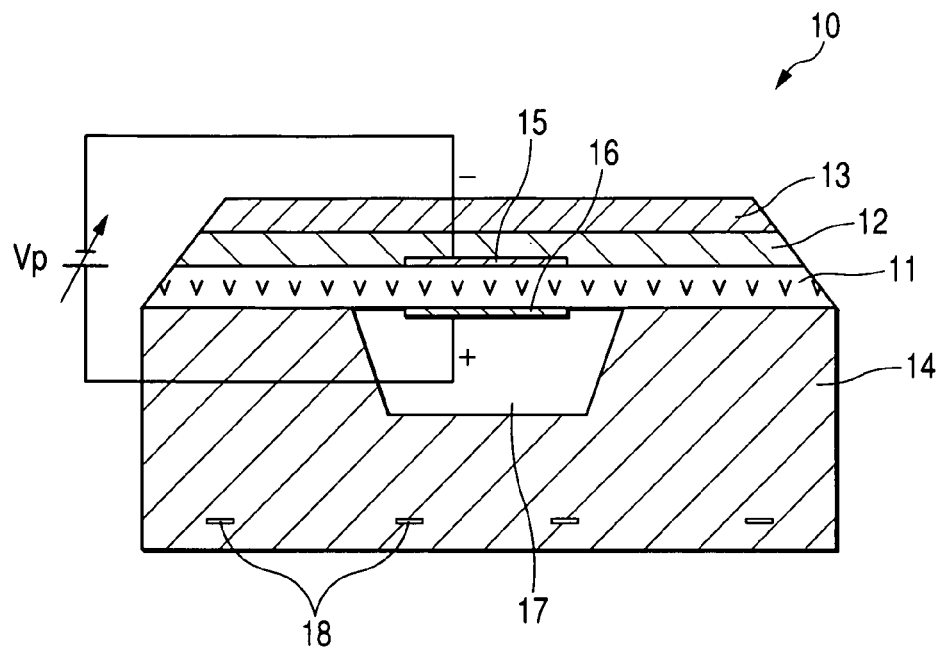
FIG. 2 is a transverse sectional view which shows a sensor element used in the gas concentration measuring apparatus as illustrated in FIG. 1.

The A/F sensor includes a laminated sensor element 10 which has a sectional structure, as illustrated in FIG. 2. The sensor element 10 has a length extending perpendicular to the drawing surface of FIG. 2 and is, in practice, disposed within a sensor housing and a protective cover. The A/F sensor is installed in an exhaust pipe of the engine. For instance, EPO 987 546 A2, assigned to the same assignee as that of this application teaches a structure and control of an operation of this type of gas sensor in detail, disclosure of which is incorporated herein by reference.

The sensor element 10 is made up of a solid electrolyte layer 11, a diffusion resistance layer 12, a shielding layer 13, and an insulating layer 14 which are laminated vertically as viewed in the drawing. The sensor element 10 is surrounded by a protective layer (not shown). The solid electrolyte layer 11 is made of a rectangular partially-stabilized zirconia sheet and has upper and lower electrodes 15 and 16 affixed to opposed surfaces thereof. The electrodes 15 and 16 are made of platinum (Pt), for example. The diffusion resistance layer 12 is made of a porous sheet which permits exhaust gasses to flow to the electrode 15. The shielding layer 13 is made of a dense sheet which inhibits the exhaust gasses from passing therethrough. The layers 12 and 13 are each formed using a sheet made of ceramic such as alumina or zirconia and have average porosities, or gas permeability different from each other.

The insulating layer 14 is made of ceramic such as alumina or zirconia and has formed therein an air duct 17 to which the electrode 16 is exposed. The insulating layer 14 has a heater 18 embedded therein. The heater 18 is made of heating wire which is supplied with power from a storage battery installed in the vehicle to produce heat the whole of the sensor element up to a desired activation temperature. In the following discussion, the electrode 15 will also be referred to as a diffusion resistance layer side electrode, and the electrode 16 will also be referred to as an atmosphere side electrode. The atmosphere side electrode 16 is connected to a positive (+) terminal of a power source, while the diffusion resistance layer side electrode 15 is connected to a negative (−) terminal of the power source.

The exhaust gasses flowing within an exhaust pipe of the engine to which the sensor element 10 is exposed enter and pass through the side of the diffusion resistance layer 12 and reach the electrode 15. When the exhaust gasses are in a fuel lean condition, oxygen molecules contained in the exhaust gasses are decomposed or ionized by application of voltage between the electrodes 15 and 16, so that they are discharged to the air duct 17 through the solid electrolyte layer 11 and the electrode 16. This will cause a positive current to flow from the atmosphere side electrode 16 to the diffusion resistance layer side electrode 15. Alternatively, when the exhaust gasses are in a fuel rich condition, oxygen molecules contained in air within the air duct 17 are ionized by the electrode 16 so that they are discharged into the exhaust pipe through the solid electrolyte layer 11 and the electrode 15 and undergo catalytic reaction with unburned components such as HC or CO in the exhaust gasses. This will cause a negative current to flow from the diffusion resistance layer side electrode 15 to the atmosphere side electrode 16.

Figure 3:
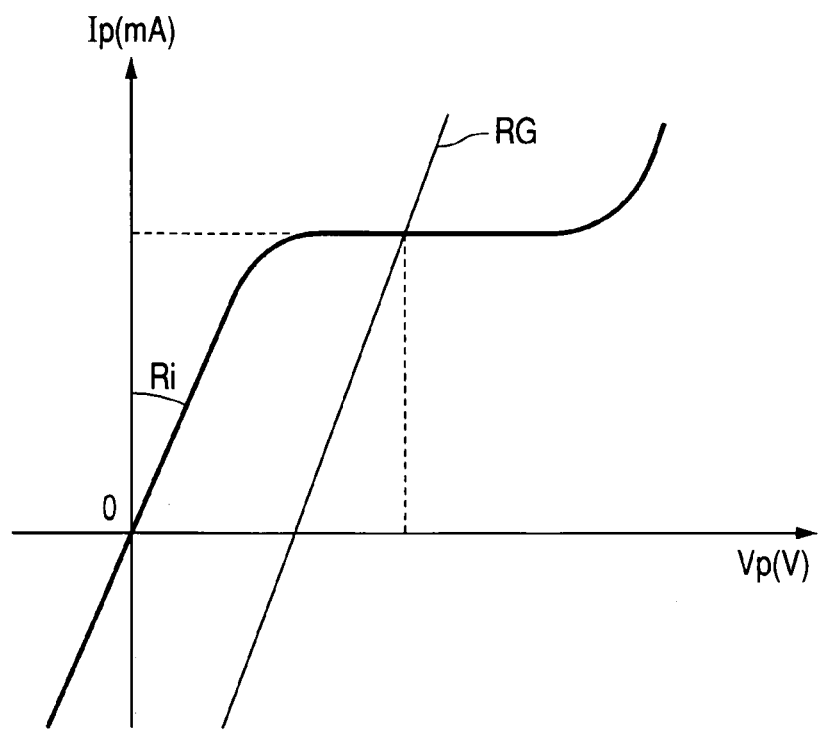
FIG. 3 shows an example of an applied voltage-to-output current map for use in determining a target voltage to be applied to the sensor element as illustrated in FIG. 2.

FIG. 3 shows a voltage-to-current relation (i.e., V-I characteristic) of the A/F sensor. A straight segment of a V-I curve extending parallel to the abscissa axis (i.e., V-axis) indicate a limiting current range within which the sensor element 10 produces an electric current Ip (i.e., a limiting current) as a function of an air-fuel ratio (i.e., richness or leanness). Specifically, as the air-fuel ratio changes to the lean side, the current Ip produced by the sensor element 10 increases, while as the air-fuel ratio changes to the rich side, the current Ip decreases. The current Ip will also be referred to as a sensor element current below.

A portion of the V-I curve lower in voltage than the limiting current range is a resistance-dependent range. An inclination of a first-order segment of the V-I curve depends upon dc internal resistance Ri of the sensor element 10. The dc internal resistance Ri changes with a change in temperature of the sensor element 10. Specifically, it increases with a decrease in temperature of the sensor element 10, so that the inclination of the first-order segment of the V-I curve in the resistance-dependent range is decreased. Alternatively, when the temperature of the sensor element 10 rises, it results in a decrease in the dc internal resistance Ri, so that the inclination of the first-order segment of V-I curve is increased. A line RG indicates a target voltage Vp to be applied to the sensor element 10 (i.e., the electrodes 15 and 16).

Referring back to FIG. 1, the gas concentration measuring apparatus, as described above, includes the engine ECU 20 which works to control an operation of the A/F sensor.

The engine ECU 20 connects with the sensor element 10 through a plus (+) terminal T1 and a minus (−) terminal T2. The terminal T1 leads to the atmosphere side electrode 16 of the sensor element 10, while the terminal T2 leads to the diffusion resistance layer side electrode 15. The engine ECU 20 also includes operational amplifiers 21 and 26, a current-measuring resistor 22, a reference voltage source 23, a voltage application control circuit 25, and an impedance detector 27. The reference voltage source 23 connects with the terminal T1 through the operational amplifier 21 and the current-measuring resistor 22. The voltage application control circuit 25 connects with the terminal T2. The voltage appearing at a junction A of an end of the current-measuring resistor 22 and the terminal T1 is kept at the same level as that of the reference voltage source 23 (i.e., a reference voltage Ref1 of 2.2 V, for example). The sensor element current Ip flows through the current-measuring resistor 22. The voltage appearing at a junction B changes with a change in the sensor element current Ip. When the exhaust gas of the engine is in a fuel lean condition, the sensor element current Ip flows from the plus terminal T1 to the minus terminal T2 through the sensor element 10, so that the voltage at the junction B rises. Alternatively, when the exhaust gas is a fuel rich condition, the sensor element current Ip flows from the minus terminal T2 to the plus terminal T1 through the sensor element 10, so that the voltage at the junction B decreases.

The voltage application control circuit 25 works to monitor the voltage at the junction B and determine the target voltage Vp to be applied to the sensor element 10 as a function of the monitored voltage, for example, by look-up using the target applying voltage line RG, as illustrated in FIG. 3. Specifically, the voltage application control circuit 25 increases the voltage to be applied to the sensor element 10 as the sensor element current Ip increases, that is, as the voltage at the junction B rises.

The operational amplifier 26 working as a differential amplifier connects with the junction B and the reference voltage source 23. An output AFO of the operational amplifier 26 is inputted as an air-fuel ratio (A/F) output voltage to an A/D (analog-to-digital) port AD1 of the CPU 30. The CPU 30 samples the A/F output voltage AFO and determines an instantaneous value of an air-fuel ratio of a mixture supplied to the engine for use in the air-fuel ratio feedback control.

The CPU 30 also works to sweep the voltage applied to the sensor element 10 instantaneously to determine a sensor element impedance Zac (i.e., an internal resistance of the sensor element 10) using a resulting change in the current Ip flowing through the sensor element 10. Specifically, when receiving a command signal from the CPU 30, the voltage application control circuit 25 enters an impedance measuring mode. The voltage application control circuit 25 then applies the voltage to the sensor element 10 and changes it in sequence by a given level (e.g., 0.2V) to the positive and negative sides. This causes the sensor element current Ip flowing through the sensor element 10 to change, thus resulting in a change in voltage developed at the junction B. The impedance detector 27 monitors the change in voltage at the junction B, calculates an impedance current by dividing the monitored change by a resistance value of the current-measuring resistor 22, and outputs it as an impedance signal Iout to an A/D port AD2 of the CPU 30. The impedance detector 27 is made up of a high-pass filter and a peak hold circuit which are connected in series and works to measure a change in ac voltage appearing at the junction B within an on-duration of a gate of the peak hold circuit (i.e., during the impedance measuring mode). The peak of the voltage at the junction B held by the peak hold circuit is reset each turning off of the gate.

The CPU 30 uses a change $\Delta V$ in voltage applied to the sensor element 10 through the voltage application control circuit 25 and a resulting change $\Delta$Iout in the impedance current signal Iout, as measured by the impedance detector 27, to determine the impedance Zac of the sensor element 10 (e.g., $\Delta V/\Delta$Iout). The determination of the sensor element impedance Zac may alternatively be made by supplying the current to the sensor element 10, sweeping it in an ac form, and monitoring a resultant change in current or voltage provided by the sensor element 10. U.S. Pat. No. 6,578,563 B2, issued Jun. 17, 2003, assigned to the same assignee as that of this application teaches how to determine the sensor element impedance Zac, disclosure of which is incorporated herein by reference.

The determination of the sensor element impedance Zac is performed at an regular time interval (e.g., 128 msec.). Specifically, the CPU 30 outputs the impedance measuring command signal to the voltage application control circuit 25 in a cycle of 128 msec. The CPU 30 also works to control an electric power supplied to the heater 18 so as to keep the sensor element impedance Zac at a given target value so that the sensor element 10 is held at a selected temperature (e.g., 750° C.) to maintain a desired activation status where the sensor element 10 produces an output as a function of the A/F ratio correctly.

The voltage appearing at the terminal T1 is also inputted as voltage VS+ to an A/D port AD3 of the CPU 30. Similarly, the voltage appearing at the terminal T2 is inputted as voltage VS− to an A/D port AD4 of the CPU 30. The voltages VS+ and VS− are used in sensor diagnosis, as will be described later in detail.

The engine ECU 20 works as a sensor failure monitor designed to monitor a failure in operation of the A/F sensor and identify the type or cause of such a failure using the signals inputted to the A/D ports AD1 to AD4. Specifically, the engine ECU 20 samples the signals inputted to the A/D ports AD1 to AD4 and compares them with those when the A/F sensor is in normal condition before and after the sensor element 10 is placed in the activation status to determine occurrence of the failure of the A/F sensor and the cause thereof.

Differences in the A/F output voltage AFO, the voltages VS+ and VS− appearing at the terminals T1 and T2, and the change $\Delta$Iout in the impedance current signal Iout before and after the sensor element 10 is placed in the activation status will be discussed below.

FIGS. 4(a) to 4(f) are time charts which demonstrate time-sequential variations in the A/F output voltage AFO, the change $\Delta$Iout, the voltages VS+ and VS−, the sensor element impedance Zac, and the temperature of the sensor element 10. The time t1 is a time when the sensor element 10 is determined to have been activated completely, for example, when the sensor element impedance Zac reaches a given activation criterion. Specifically, before time t1, the sensor element 10 is determined not to be activated yet, while after time t1, the sensor element 10 is determined to have been activated completely.

Before the sensor element 10 is heated and activated, the sensor element impedance Zac has, as illustrated in FIG. 4(e), an infinite value, so that no current flows through the sensor element 10. This causes the A/F output voltage AFO to be kept at the same level as the reference voltage Ref1 (i.e., 2.2V). In this case, when the voltage applied to the sensor element 10 is swept in the ac form to measure the sensor element impedance Zac, it results in no change in resultant current through the sensor element 10. The change ΔIout in the impedance current signal Iout, as illustrated in FIG. 4(*b*), is still zero (0). The voltage VS+ at the terminal T1 is 2.2V equal to the reference voltage Ref1. The voltage VS− at the terminal T2 is kept at, for example, 1.8V corresponding to the stoichiometric air-fuel ratio (which will also be referred to as a stoichiometric point below).

Afterwards, when the sensor element 10 begins increasing in temperature, the sensor element impedance Zac drops gradually. When the sensor element impedance Zac reaches the activation criterion at time t1, the CPU 30 determines that the sensor element 10 has been activated completely. When activated, the sensor element 10 produces a flow of the current Ip which converges the A/F output voltage AFO at a value corresponding to instantaneous exhaust gas atmosphere of the engine. FIGS. 4(*a*) to 4(*f*) demonstrate for cases where the exhaust gas is extremely lean (corresponding to the atmospheric air), lean (e.g., A/F=18), and in a stoichiometric state (e.g., A/F=12). The A/F output voltage AFO rises in level in a region leaner than the stoichiometric A/F ratio, while it drops in a rich region. In a region from an A/F ratio of 12 to an A/F ratio corresponding to the atmospheric air that is an A/F ratio measurable range, the A/F output voltage AFO varies approximately between 1.6 to 4.1V.

The change ΔIout in the impedance current signal Iout varies as the sensor element impedance Zac decreases (i.e., the temperature of the sensor element 10 increases) and then converges at a constant value when the sensor element 10 reaches the activation status.

The voltage VS+ at the terminal T1 is held at 2.2V even after the sensor element 10 is placed in the activation status, while the voltage VS− at the terminal T2 varies as a function of the current flowing through the sensor element 10 under control of the voltage application control circuit 25. The voltage application control circuit 25 works to increase the voltage to be applied to the sensor element 10 as the exhaust gas is leaner, so that the voltage VS− drops in the lean region (less than 1.8V), while the voltage VS+ rises in the rich region.

When the A/F sensor is operating normally, the A/F output voltage AFO, the change ΔIout, and the voltages VS+ and VS− vary, as illustrated in FIGS. 4(*a*) to 4(*d*), as the activation of the sensor element 10 progresses. When the A/F sensor is malfunctioning, the A/F output voltage AFO, the change ΔIout, the voltages VS+ and VS− experience variations different from normal ones. The variations in the A/F output voltage AFO, the change ΔIout, the voltages VS+ and VS− arising from the following six typical causes of failure in operation of the A/F sensor will be discussed below.

(a) sensor wire breakage (b) VB short of terminal T1

(c) GND short of terminal T1

(d) VB short of terminal T2

(e) GND short of terminal T2

(f) T1-to-T2 terminal short

The first cause (a) is disconnection of the terminal T1 or T2. The second cause (b) is an electric short of the terminal T1 to the battery. The third cause (c) is an electric short of the terminal T1 to ground. The fourth cause (d) is an electric short of the terminal T2 to the battery. The fifth cause (e) is an electric short of the terminal T2 to ground. The sixth cause (f) is an electrical short between the terminals T1 and T2.

The inventors of this application measured the A/F output voltage AFO, the change ΔIout, and the voltages VS+ and VS− in the events of the above six causes (a) to (f) of failure of the A/F sensor. The measured values are shown in a table of FIG. 5.

The last row of the table indicates values of the A/F output voltage AFO, the change ΔIout, and the voltages VS+ and VS− when the A/F sensor is operating properly. "○" in cells represents a case where the A/F sensor is determined to be malfunctioning. "X" in cells represents a case where the A/F sensor is determined to be operating normally. The values before the activation of the sensor element 10 are what were measured immediately after the A/F sensor is turned on (i.e., the engine starts up), while the values after the activation of the sensor element 10 are what were measured one (1) minute after the A/F sensor is turned on in order to avoid measurement in transition of the activation of the sensor element 10.

Sensor Wire Breakage

If the wire breakage occurs in the A/F sensor, the change ΔIout in the impedance current signal Iout is kept zero (0) before and after the activation of the sensor element 10. The change ΔIout before the activation of the sensor element 10 is identical with that when the A/F sensor is operating normally, but has a value different from the normal one after the activation of the sensor element 10. The same is true for the failure types (b) to (f), and explanation thereof will be omitted in the following discussion on the failure causes (b) to (f).

The A/F output voltage AFO is kept at the reference voltage of 2.2V before and after the activation of the sensor element 10. The value of the A/F output voltage AFO before the activation of the sensor element 10 is identical with that when the A/F sensor is operating normally. The value of the A/F output voltage AFO after the activation of the sensor element 10 lies within a normal range of 1.6 to 4.1V. The voltage VS+ at the terminal T1 is kept at the reference voltage of 2.2V before and after the activation of the sensor element 10. The voltage VS− at the terminal T2 is kept at a constant value of 1.8V before and after the activation of the sensor element 10.

VB Short of Terminal T1

If the terminal T1 is short-circuited to a battery (i.e., a power supply) installed in the vehicle, a battery output voltage of, for example, 14V is applied to the terminal T1. This causes the A/F output voltage AFO and the voltage VS+ appearing at the terminal T1 to be fixed at 5.0V that is an upper limit of an input signal voltage range of the CPU 30 before and after the activation of the sensor element 10. Typical CPUs are designed to receive an input at a maximum of 5V or 12V. In a case of 12V, the A/F output voltage AFO and the voltage VS+ are fixed at 12V. Alternatively, in a case of 5.0V, the A/F output voltage AFO and the voltage VS+ are fixed at 5.0V.

In the structure of FIG. 1, if the terminal T1 is short-circuited, both voltages developed at the junctions A and B across the current-measuring resistor 22 rise, thereby causing the A/F output voltage AFO and the voltage VS+ to be fixed at 5.0V. The voltage VS− appearing at the terminal T2 before the activation of the sensor element 10 is kept at 1.8V, but rises, like the voltage VS+, up to 5.0V due to a drop in the sensor element impedance Zac after the activation of the sensor element 10.

GND Short of Terminal T1

If the terminal T1 is short-circuited to ground, a ground potential of zero (0V) appears at the terminal T1. This causes the voltage VS+ at the terminal T1 to be kept at 0V before and after the activation of the sensor element 10. The voltage at the junction A (i.e., the end of the current-measuring resistor 22) is, thus, at 0V. The operational amplifier 21 works to produce a maximum current to elevate the voltage at the junction A up to the reference voltage of 2.2V, so that the voltage at the junction B rises. This causes the A/F output voltage AFO and the voltage VS+ to be fixed at 5.0V that is the upper limit of the input signal voltage range of the CPU 30 before and after the activation of the sensor element 10. The voltage VS- appearing at the terminal T2 before the activation of the sensor element 10 is kept at 1.8V and rises up to the voltage at the junction B (i.e., 5.0V) after the activation of the sensor element 10, but lowered ultimately by the activation of the voltage application control circuit 25 to 0.9V that is a lower output limit of the voltage application control circuit 25.

VB Short of Terminal T2

If the terminal T1 is short-circuited to the battery, a battery voltage of, for example, 14V is applied to the terminal T2. This the voltage VS-+appearing at the terminal T2 to be fixed at 5.0V that is the upper limit of the input signal voltage range of the CPU 30 before and after the activation of the sensor element 10. Before the activation of the sensor element 10, the sensor element impedance Zac is infinite, so that the voltage VS+ at the terminal T1 is insensitive to the short of the terminal T2, thereby causing the A/F output voltage AFO and the voltage VS+ at the terminal T1 to be kept at the reference voltage of 2.2V. After the activation of the sensor element 10, the sensor element impedance Zac drops, so that the voltage VS+ at the terminal T1 rises, like the terminal 72, thus causing the A/F output voltage AFO and the voltage VS+ to increase up to 5.0V that is the upper limit of the input signal voltage range of the CPU 30.

GND Short of Terminal T2

If the terminal 72 is short-circuited to ground, a ground potential of zero (0V) will appear at the terminal T2. This causes the voltage VS- appearing at the terminal T2 to be kept at 0V before and after the activation of the sensor element 10. Before the activation of the sensor element 10, the sensor element impedance Zac is substantially infinite (Zac=∞), so that the voltage VS+ at the terminal T1 is insensitive to the short of the terminal T2, thereby causing the A/F output voltage AFO and the voltage VS+ at the terminal T1 to be kept at the reference voltage of 2.2V. With progress in the activation of the sensor element 10, the sensor element impedance Zac decreases, so that the voltage VS+ at the terminal T1 is increased up to 5.0V that is the upper limit of the input signal voltage range of the CPU 30. After completion of the activation of the sensor element 10, the voltage VS+ is held at 5.0V.

T1-to-T2 Terminal Short

If a short occurs between the terminals T1 and T2, it will cause an excessive current to flow through the current-measuring resistor 22, so that the A/F output voltage AFO is kept at 5.0V that is the upper limit of the input signal voltage range of the CPU 30. The same is true for before and after the activation of the sensor element 10. The rise in voltage at the junction B causes the voltage application control circuit 25 to operate to adjust the voltage to be applied to the sensor element 10 to a lower limit (e.g., 1.1V) of an applied-voltage control range of the voltage application control circuit 25 (i.e., the lowest voltage to be applied to the sensor element 10 within the lean region), so that the voltage VS- developed at the terminal T2 will be the lower limit (1.1V) of the applied-voltage control range. The voltage VS+ at the terminal T1 will be placed at the same potential (1.1V) as the voltage VS-.

The value within the applied-voltage control range of the application voltage control circuit 25 at which the voltages VS+ and VS- is placed in the voltage VS- in the event of the T1-to-T2 terminal short depends upon a difference in current control capability between the operational amplifier 21 leading to the terminal T1 and an operational amplifier installed in the voltage application control circuit 25 leading to the terminal T2. In the structure of FIG. 1, the operational amplifier of the voltage application control circuit 25 is superior in the current control capability than the operational amplifier 21, so that the voltages VS+ and VS- are placed at the lean limit (i.e., 1.1V) of the applied-voltage control range of the voltage application control circuit 25. If the operational amplifier 21 is superior in the current control capability, the voltages VS+ and VS- are placed at a maximum of 2.2V.

As apparent from the above discussion, in the event of failure of the A/F sensor, the A/F output voltage AFO, the change ΔIout, the voltages VS+ and VS- have values different from normal ones depending upon the cause of the failure. The cause of failure occurring at the A/F sensor may, thus, be identified by monitoring a combination of the values of the A/F output voltage AFO, the change ΔIout, the voltages VS+ and V-.

We analyzed the values in FIG. 5 and found that the A/F output voltage AFO has the same value of 5.0V in the events of the VB short of the terminal T1, the GND short of the terminal T1, and the T1-to-T2 short before and after the activation of the sensor element 10 and also has the same value of 2.2V before the activation of the sensor element 10 and 5.0V after the activation of the sensor element 10 in the events of the VB short of the terminal T2 and the GND short of the terminal T2. The discrimination among following three causes of failure of the A/F sensor may, therefore, be achieved by analyzing the change ΔIout in the impedance current signal Iout and the A/F output voltage AFO.

(a1) sensor wire breakage
(b1) VB or GND short of terminal T1 or T1-to-T2 short
(c1) VB or GND short of terminal T2

FIG. 6 is table which demonstrates values of the change ΔIout in the impedance current signal Iout and the A/F output voltage AFO in the events of the above three causes (a1), (b1), and (c1) of failure of the A/F sensor. The table shows that a determination of whether the A/F sensor is failing in operation or not after the activation of the sensor element 10 may be made by comparing the value of the change ΔIout in the impedance current signal Iout with a normal one, and a discrimination among the three causes of failure of the A/F sensor in such an event may be made by comparing values of the A/F output voltage AFO before and after the activation of the sensor element 10 with normal ones.

Figure 7:
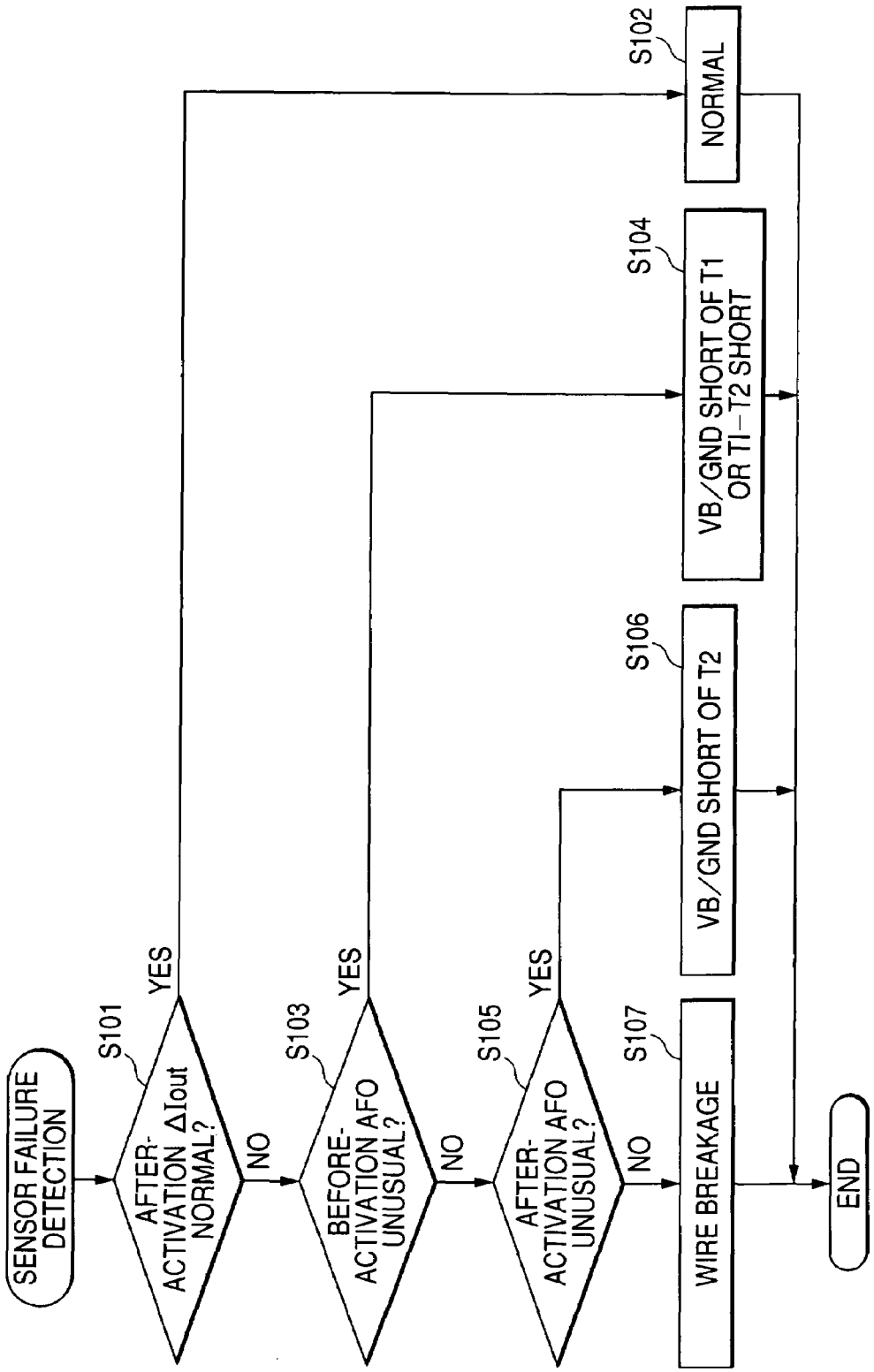
FIG. 7 is a flowchart of a program to be executed to detect and identify the cause of failure in an A/F sensor.

FIG. 7 is a flowchart of a sequence of logical steps or program to be executed by the CPU 30 to monitor a failure in operation of the A/F sensor.

The program is initiated after the engine is started up, the A/F output voltage AFO is measured before the activation of the sensor element 10, and the A/F output voltage AFO and the change ΔIout in the impedance current signal Iout are measured after the activation of the sensor element 10. The values of the A/F output voltage AFO and the change ΔIout in the impedance current signal Iout are sampled at times other than during transition of the activation of the sensor element 10 in order to distinguish the sampled values clearly before and after the activation of the sensor element 10.

First, in step 101, it is determined whether the value of the change ΔIout in the impedance current signal Iout, as sampled after the activation of the sensor element 10 is identical with a normal one or not. If a YES answer is obtained, then the routine proceeds to step 102 wherein it is determined that the A/F sensor is operating properly. Alternatively, if a NO answer is obtained meaning that the A/F sensor is malfunctioning, then the routine proceeds to step 103 wherein it is determined whether the value of the A/F output voltage AFO, as sampled before the activation of the sensor element 10, is different from a normal one or not. If a YES answer is obtained, then the routine proceeds to step 104 wherein it is determined that at least one of the VB short and GND short of the terminal T1 and the T1-to-T2 short has occurred. Alternatively, if a NO answer is obtained, then the routine proceeds to step 105 wherein the value of the A/F output voltage AFO, as sampled after the activation of the sensor element 10, is different from a normal one or not. If a YES answer is obtained, then the routine proceeds to step 106 wherein it is determined that at least one of the VB short and GND short of the terminal T2 has occurred. Alternatively, if a NO answer is obtained in step 105 meaning that the values of the A/F output voltage AFO, as sampled before and after the activation of the sensor element 10, are both normal, then the routine proceeds to step 107 wherein it is determined that the sensor wire breakage has occurred.

As apparent from the above discussion, the CPU 30 works as a sensor failure monitor designed to analyze the values of the A/F output voltage AFO, as sampled before and after the activation of the sensor element 10 and the value of the change ΔIout in the impedance current signal Iout, as sampled after the activation of the sensor element 10, to identify the cause of failure in operation of the A/F sensor or discriminate at least among the three types of causes (a1), (b1), and (c1), as described above, of failure of the A/F sensor. The CPU 30 uses the signals inputted only to the A/D ports AD1 and AD2 to monitor the failure of the A/F sensor and may, thus, be designed not to have the A/D ports AD3 and AD4 in order to simplify the overall structure thereof.

The second embodiment of the CPU 30 will be described below.

The CPU 30 of this embodiment is designed to also use the voltage VS+ appearing at the terminal T1 in addition to the A/F output voltage AFO and the change ΔIout in the impedance current signal Iout to discriminate among all the types of causes (a) to (f), as described above, of failure of the A/F sensor.

FIG. 8 is a table which demonstrates values of the change Δ Iout in the impedance current signal Iout, the A/F output voltage AFO, and the voltage VS+ at the terminal T1, as sampled before and after the activation of the sensor element 10 in the events of the six types of causes (a) to (f) of failure of the A/F sensor.

The table shows that the A/F output voltage AFO has the same value of 5.0V before and after the activation of the sensor element 10 in the events of the VB short and GND short of the terminal T1 and T1-to-12 short, but the voltage VS+ have different values of 5.0, 0, and 1.1V. The discrimination among these three types of causes of failure of the A/F sensor may, thus, be made by analyzing the value of the voltage VS+ appearing at the terminal T1. The table also shows that the A/F output voltage AFO has the same value of 5.0V before and after the activation of the sensor element 10 in the events of the VB short and GND short of the terminal T2, but the voltage VS+ have different values. The discrimination between these two types of causes of failure of the A/F sensor may also be achieved by analyzing the value of the voltage VS+ appearing at the terminal T1.

Figure 9:
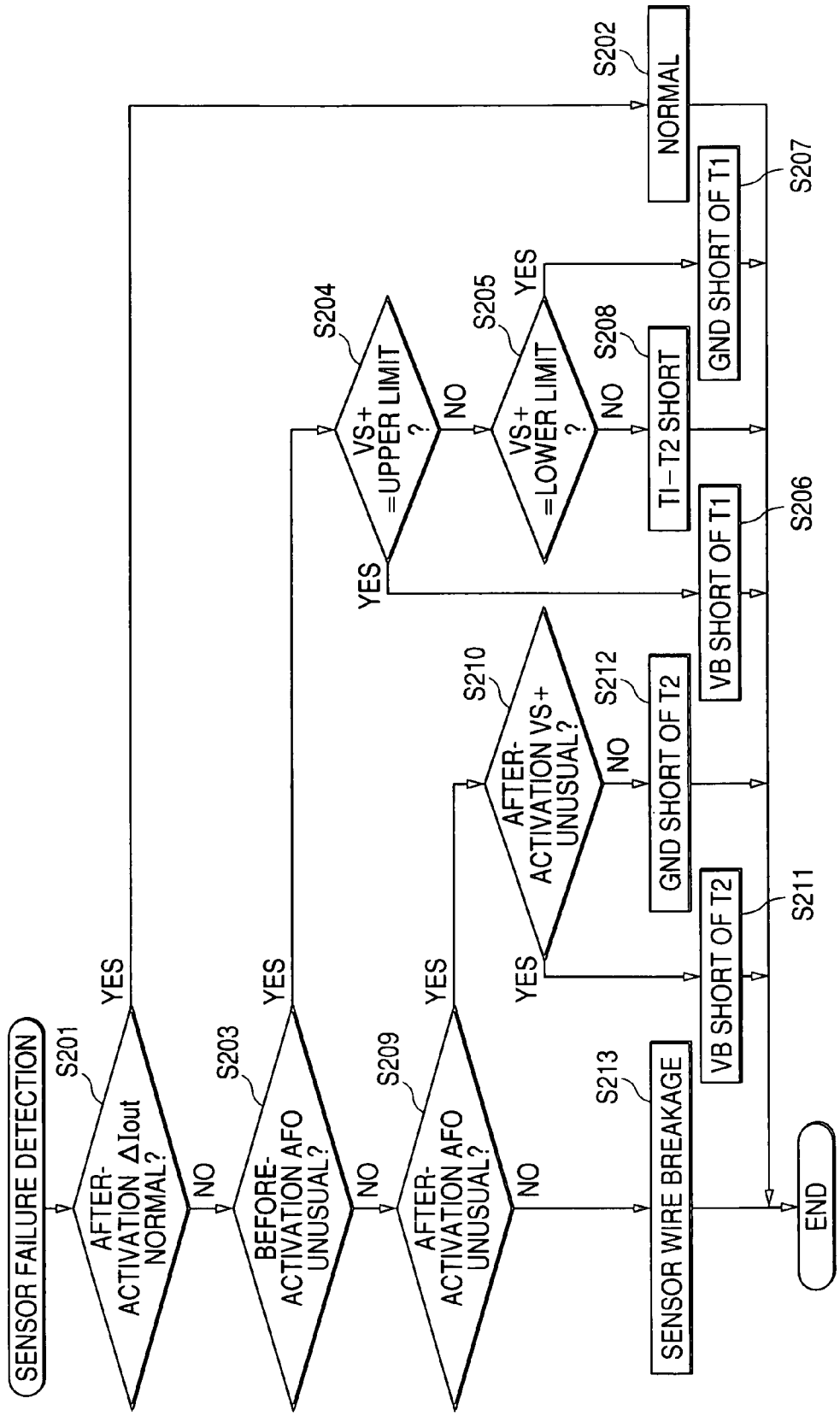
FIG. 9 is a flowchart of a program to be executed to detect and identify the cause of failure in an A/F sensor using the table of FIG. 8.

FIG. 9 is a flowchart of a program to be executed by the CPU 30 to discriminate among the six types of causes (a) to (f) of failure of the A/F sensor in the second embodiment. The program is, like the first embodiment, initiated after the engine is started up, the A/F output voltage AFO is measured before the activation of the sensor element 10, and the A/F output voltage AFO, the change ΔIout in the impedance current signal Iout, and the voltage VS+ appearing at the terminal T1 are measured after the activation of the sensor element 10.

After entering the program, the routine proceeds to step 201 wherein it is determined whether the value of the change ΔIout in the impedance current signal Iout, as sampled after the activation of the sensor element 10 is identical with a normal one or not. If a YES answer is obtained, then the routine proceeds to step 202 wherein it is determined that the A/F sensor is operating properly. Alternatively, if a NO answer is obtained meaning that the A/F sensor is malfunctioning, then the routine proceeds to step 203 wherein it is determined whether the value of the A/F output voltage AFO, as sampled before the activation of the sensor element 10, is different from a normal one or not. If a YES answer is obtained, then the routine proceeds to step 204 wherein it is determined whether the voltage VS+ is equal to the upper limit thereof (i.e., 5.0V) or not. If a NO answer is obtained, then the routine proceeds to step 205 wherein it is determined whether the voltage VS+ is equal to the lower limit thereof (i.e., 0V) or not. As can be seen from FIG. 8, if the A/F output voltage AFO, as sampled before the activation of the sensor element 10, has an unusual value, the voltage VS+ has the same value before and after the activation of the sensor element 10. The value of the voltage VS+ either before or after the activation of the sensor element 10 may, therefore, be used in steps 204 and 205, but, the one after the activation of the sensor element 10 is used in this embodiment.

If a YES answer is obtained in step 204 meaning that the voltage VS+ is equal to the upper limit thereof (i.e., 5.0V), then the routine proceeds to step 206 wherein it is determined that the VB short of the terminal T1 has occurred. If a YES answer is obtained in step 205 meaning that the voltage VS+ is equal to the lower limit thereof (i.e., 0V), then the routine proceeds to step 207 wherein it is determined that the GND short of the terminal T1 has occurred. Alternatively, if a NO answer is obtained in step 205, then the routine proceeds to step 208 wherein it is determined that the T1-to-T2 short has occurred.

If a NO answer is obtained in step 203 meaning that the A/F output voltage AFO, as sampled before the activation of the sensor element 10, has a normal value, then the routine proceeds to step 209 wherein it is determined whether the value of the A/F output voltage AFO, as sampled after the activation of the sensor element 10, is different from a normal one or not. If a YES answer is obtained, then the routine proceeds to step 210 wherein it is determined whether the voltage VS+, as sampled after the activation of the sensor element 10, has an unusual value or not. If a YES answer is obtained, then the routine proceeds to step 211 wherein it is determined that the VB short of the terminal T2 has occurred. Alternatively, if a NO answer is obtained, then the routine proceeds to step 212 wherein it is determined that the VB short of the terminal T1 has occurred.

If a NO answer is obtained in step 209 meaning that the values of the A/F output voltage AFO, as sampled before and after the activation of the sensor element 10, are both normal, then the routine proceeds to step 213 wherein it is determined that the sensor wire breakage has occurred.

As apparent from the above discussion, the CPU 30 of the second embodiment works to analyze three failure-detecting parameters: the values of the A/F output voltage AFO, the change Δ Iout in the impedance current signal Iout, and the voltage VS+ appearing at the terminal T1 inputted to the A/D ports AD1, AD2, and AD3 and may, thus, be designed not to have the A/D port AD4 in order to simplify the overall structure thereof.

The third embodiment of the CPU 30 will be described below which is designed to discriminate among the six types of causes (a) to (f) of failure of the A/F sensor using the change ΔIout in the impedance current signal Iout and the voltage VS− appearing at the terminal T2 to which the current-measuring resistor 22 is not connected.

FIG. 10 is a table which demonstrates values of the change Δ Iout in the impedance current signal Iout and the voltage VS− appearing at the terminal T2 as sampled before and after the activation of the sensor element 10 in the events of the six types of causes (a) to (f) of failure of the A/F sensor.

Figure 11:
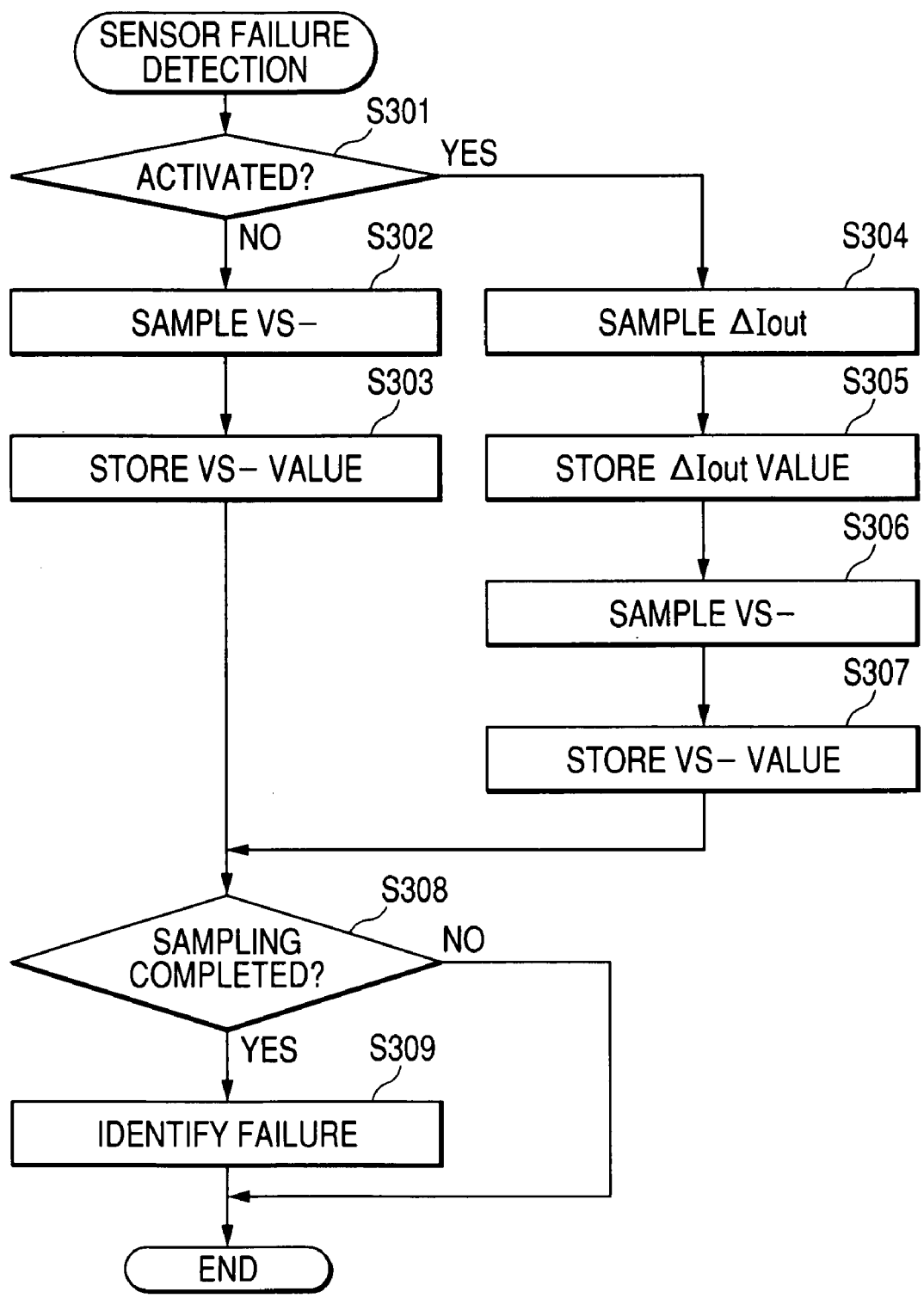
FIG. 11 is a flowchart of a program to be executed to detect and identify the cause of failure in an A/F sensor using the table of FIG. 10.

FIG. 11 is a flowchart of a program to be executed by the CPU 30 to discriminate among the six types (a) to (f) of causes of failure of the A/F sensor in the third embodiment. The program is performed instead of the ones as illustrated in FIGS. 7 and 9.

After entering the program, the routine proceeds to step 301 wherein it is determined that the sensor element 10 has been activated completely or not. If a NO answer is obtained, then the routine proceeds to step 302 wherein the value of the voltage VS− at the terminal T2 is sampled. The routine proceeds to step 303 wherein the value of the voltage VS−, as sampled in step 302, is compared with a normal one, and a result of the comparison is stored in a memory built in the CPU 30.

If a YES answer is obtained in step 301, then the routine proceeds to step 304 wherein the value of the change ΔIout in the impedance current signal Iout is sampled. The routine proceeds to step 305 wherein the value of the change ΔIout, as sampled in step 304, is compared with a normal one, and a result of the comparison is stored in the memory. The routine proceeds to step 306 wherein the value of the voltage VS− at the terminal T2 is sampled. The routine proceeds to step 307 wherein the value of the voltage VS−, as sampled in step 306, is compared with a normal one, and a result of the comparison is stored in the memory.

After step 303 or 307, the routine proceeds to step 308 wherein all data, as required to identify the cause of failure of the A/F sensor, have been sampled or not. If a YES answer is obtained, then the routine proceeds to step 309 wherein the values of the change ΔIout and the voltage VS− are read out of the memory to identify the cause of failure of the A/F sensor. Specifically, a combination of the values of the change ΔIout and the voltage VS− is looked up from the table of FIG. 10 to discriminate among the causes (a) to (f) of failure of the A/F sensor in a similar manner, as described in the first and second embodiments.

The CPU 30 of the third embodiment works to analyze two failure-detecting parameters: the values of the change ΔIout in the impedance current signal Iout and the voltage VS− appearing at the terminal T2 inputted to the A/D ports AD2 and AD4 and may, thus, be designed not to have the A/D ports AD1 and AD3 in order to simplify the overall structure thereof.

In the program of FIG. 11, a determination of whether the A/F sensor is failing in operation or not may be first made using the value of the change ΔIout in the impedance current signal Iout, as sampled after the activation of the sensor element 10. When the A/F sensor is determined as being failing in operation, the cause of failure of the A/F sensor may be identified using the value of the voltage VS−.

Figure 12:
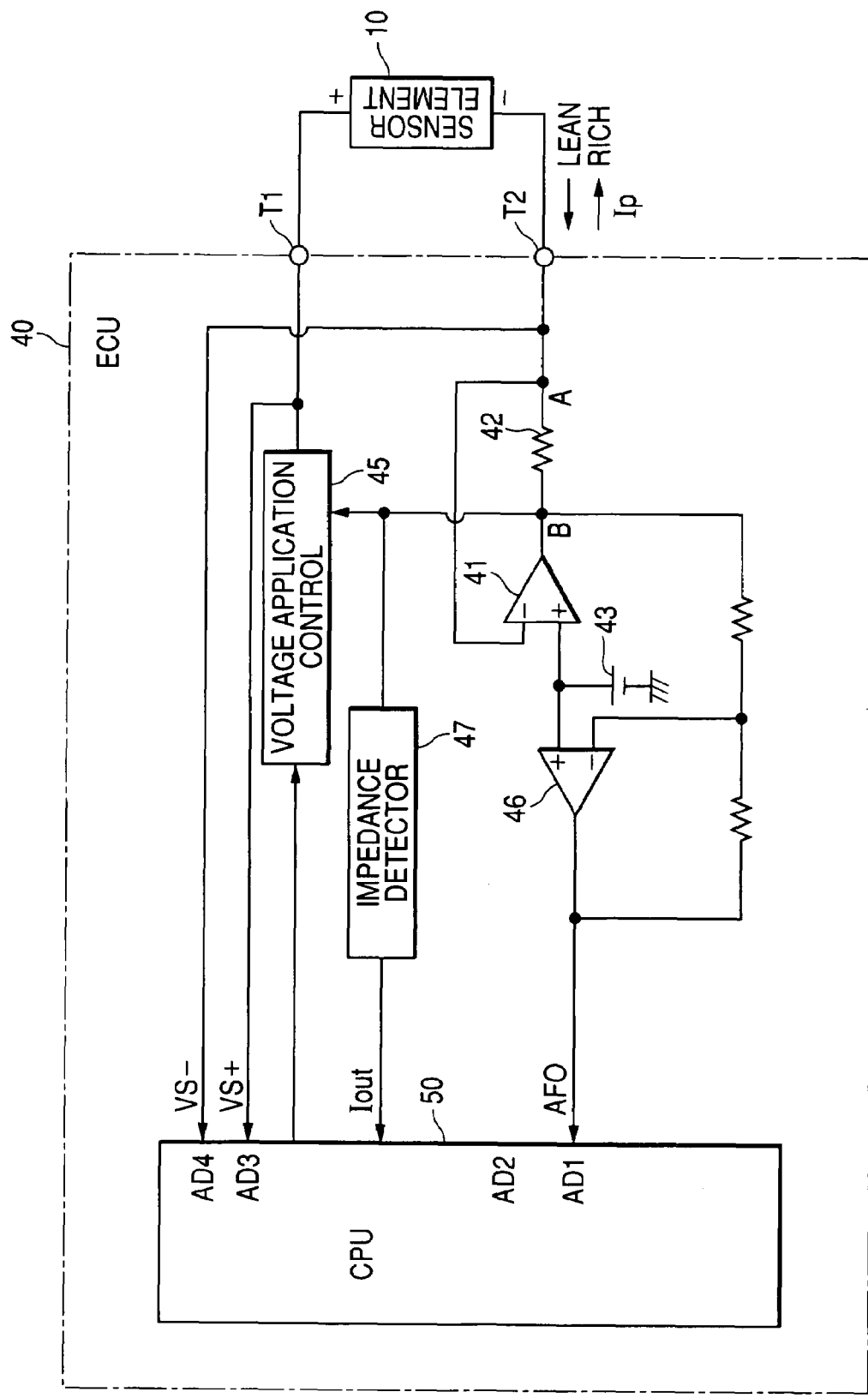
FIG. 12 is a circuit diagram which shows an electric structure of a gas concentration measuring apparatus according to the fourth embodiment of the invention.

FIG. 12 shows an engine ECU 40 according to the fourth embodiment of the invention which has the structure in which circuit components leading to the terminals T1 and T2 are reversed to those of the ECU 20 in FIG. 1.

The ECU 40 includes operational amplifiers 41 and 46, a current-measuring resistor 42, a reference voltage source 43, a voltage application control circuit 45, and an impedance current detector 47.

The reference voltage source 43 connects with the terminal T2 through the operational amplifier 41 and the current-measuring resistor 42. The voltage application control circuit 45 connects with the terminal T1. The voltage appearing at the junction A of the current-measuring resistor 42 and the terminal T2 is kept at the same level as that of the reference voltage source 23 (e.g., 2.2 V). The sensor element current Ip flows through the current-measuring resistor 42. The voltage appearing at the junction B of the current-measuring resistor 42 and the operational amplifier 41 changes with a change in the sensor element current Ip. When the exhaust gas of the engine is in the fuel lean condition, the sensor element current Ip flows from the terminal T1 to the terminal T2 through the sensor element 10, so that the voltage at the junction B drops. Alternatively, when the exhaust gas is the fuel rich condition, the sensor element current Ip flows from the terminal T2 to the terminal T1 through the sensor element 10, so that the voltage at the junction B rises.

The voltage application control circuit 45 works to monitor the voltage at the junction B and determine a target voltage to be applied to the sensor element 10 as a function of the monitored voltage, for example, by look-up using the target applying voltage line RG, as illustrated in FIG. 3. Specifically, the voltage application control circuit 45 increases the voltage to be applied to the sensor element 10 as the sensor element current Ip increases, that is, as the voltage at the junction B decreases.

The operational amplifier 46 working as a differential amplifier is connected to the junction B and the reference voltage source 43. The output AFO of the operational amplifier 46 is inputted as an air-fuel ratio (A/F) output voltage to the A/D port AD1 of the CPU 50. The CPU 50 samples the A/F output voltage AFO and determines an instantaneous value of an air-fuel ratio of mixture supplied to the engine. When the time the sensor element impedance Zac should be determined is reached, the voltage application control circuit 45 is responsive to a command signal from the CPU 50 to change the voltage applied to the sensor element 10 sequentially by a given level (e.g., 0.2V) to the positive and negative sides. The impedance current detector 47 monitors a resultant change in voltage at the junction B and outputs the impedance current signal Iout to the A/D port AD2 of the CPU 50.

The voltage VS+ appearing at the terminal T1 is inputted to the A/D port AD3 of the CPU 50. The voltage VS− appearing at the terminal T2 is inputted to the A/D port AD4 of the CPU 50.

FIG. 13 demonstrate values of the change ΔIout in the impedance current signal Iout, the A/F output voltage AFO, and the voltages VS+ and VS− appearing at the terminals T1 and T2 in the events of the above six types of causes (a) to (f) of failure of the A/F sensor in the fourth embodiment. Most of listed parameters are substantially identical with those in FIG. 5, and explanation thereof in detail will be omitted here.

The CPU 50 employs the following three combinations of the failure-detecting parameters in FIG. 13 to identify the failure of the A/F sensor.

(1) change ΔIout and A/F output voltage AFO (2) change ΔIout, A/F output voltage AFO, and voltage VS−

(3) change ΔIout and voltage VS+

The parameter combination (1) is used to detect the following four types of causes of failure of the A/F sensor.
(a2) sensor wire breakage
(b2) VB or GND short of terminal T1
(c2) VB or GND short of terminal T2
(d2) T1-to-T2 short The parameter combinations (2) and (3) are used to detect the following six types of causes of failure of the A/F sensor.
(a) sensor wire breakage
(b) VB short of terminal T1
(c) GND short of terminal T1
(d) VB short of terminal T2
(e) GND short of terminal T2
(f) T1-to-T2 short The identification of the type of cause of failure of the A/F sensor using the above parameter combinations may be accomplished in substantially the same manner as described in the above embodiments, and explanation thereof in detail will be omitted here.

In the structure of FIG. 12, the current-measuring resistor 22 and the voltage application control circuit 25 may also provided in connection with either one of the terminals T1 and T2.

Figure 14:
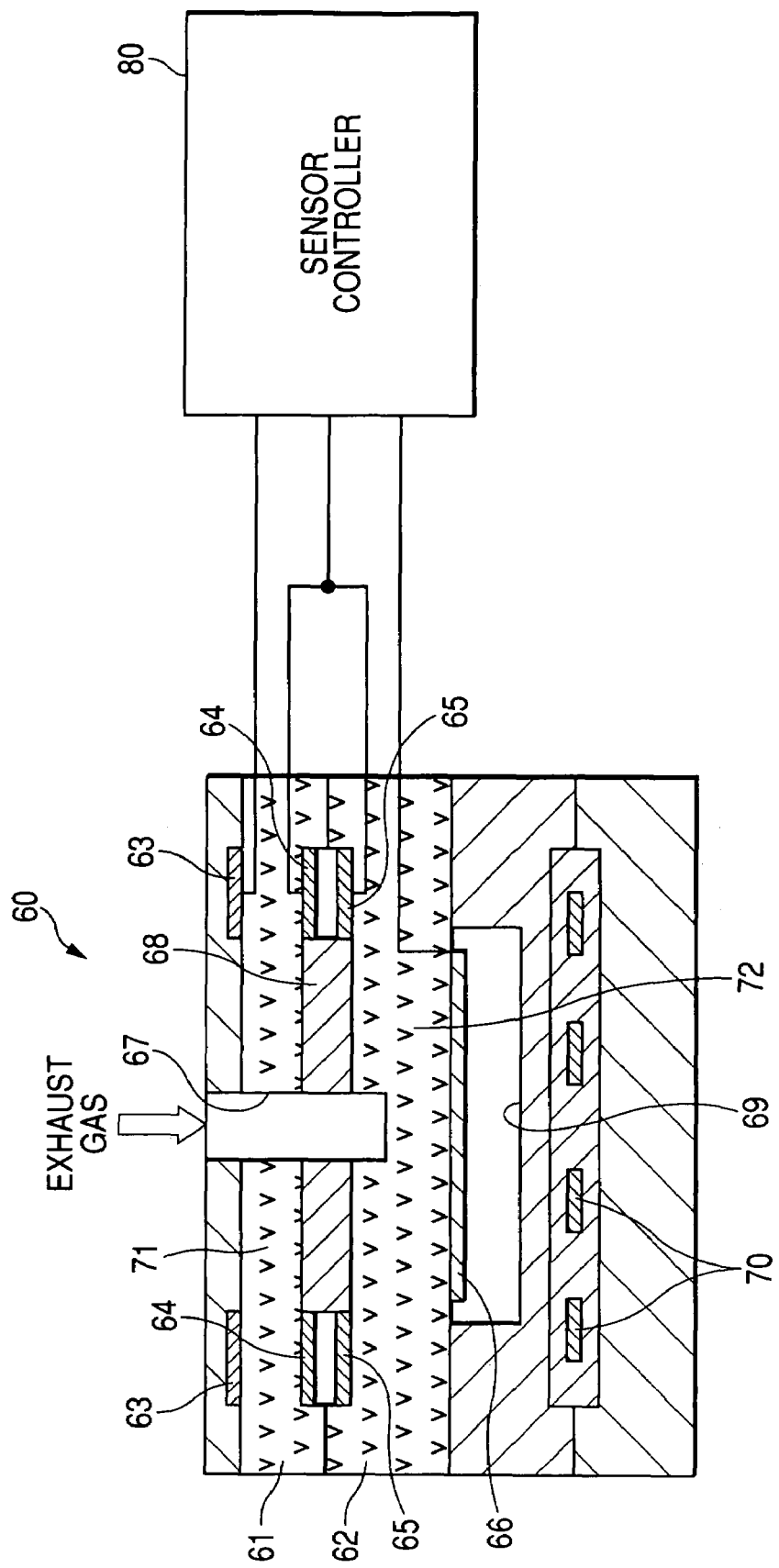
FIG. 14 a transverse sectional view which shows a sensor element of a gas concentration measuring apparatus according to the fifth embodiment of the invention.

FIG. 14 shows a sensor element 60 according to the fifth embodiment of the invention which is different in structure from the one illustrated in FIG. 2 and may be fabricated in the A/F sensor as used in each of the above embodiments instead of the sensor element 10.

The sensor element 60 includes two solid electrolyte layers 61 and 62. The solid electrolyte layer 61 has electrodes 63 and 64 affixed to opposed surfaces thereof. Similarly, the solid electrolyte layer 62 has electrodes 65 and 66 affixed to opposed surfaces thereof. Each of the electrodes 63, 64, and 65 is viewed in the drawing as being made up of right and left separate parts, but, it is, in practice, formed by a single plate having a connecting portion (not shown) extending in a transverse direction in the drawing.

The solid electrolyte layer 61 and the electrodes 63 and 64 constitute a pump cell 71. The solid electrolyte layer 62 and the electrodes 65 and 66 constitute a monitor cell 72. The electrodes 63 to 66 are joined to a sensor control circuit 80 which leads to the CPU 30, as illustrated in FIG. 1. The sensor element 60 is identical in a laminated structure with the sensor element 10.

The sensor element 60 also includes a gas inlet 67 through which exhaust gasses of the automotive engine enter and a porous diffusion layer 68, an air duct 69, and a heater 70. The structure and operation of this type of sensor element are disclosed in, for example, U.S. Pat. No. 6,295,862 B1, assigned to the same assignee as that of this application, disclosure of which is incorporated herein by reference. The monitor cell 72 is generally also called an electromotive force cell or an oxygen concentration sensor cell.

The monitor cell 72 works to produce an electromotive force which has one of two discrete values (e.g., 0V and 0.9V) selectively as a function of whether the exhaust gasses are on the rich side or the lean side of a stoichiometric point corresponding to a stoichiometric air-fuel ratio of mixture supplied to the engine. When the exhaust gasses are on the lean side, the monitor cell 72 produces a lower electromotive force. Conversely, when the exhaust gasses are on the rich side, the monitor cell 72 produces a higher electromotive force. The voltage application control circuit 25 works to control the voltage applied to the pump cell 71 so that an electromotive force produced by the monitor cell 72 is kept at 0.45V which corresponds to the stoichiometric point.

Figure 15:
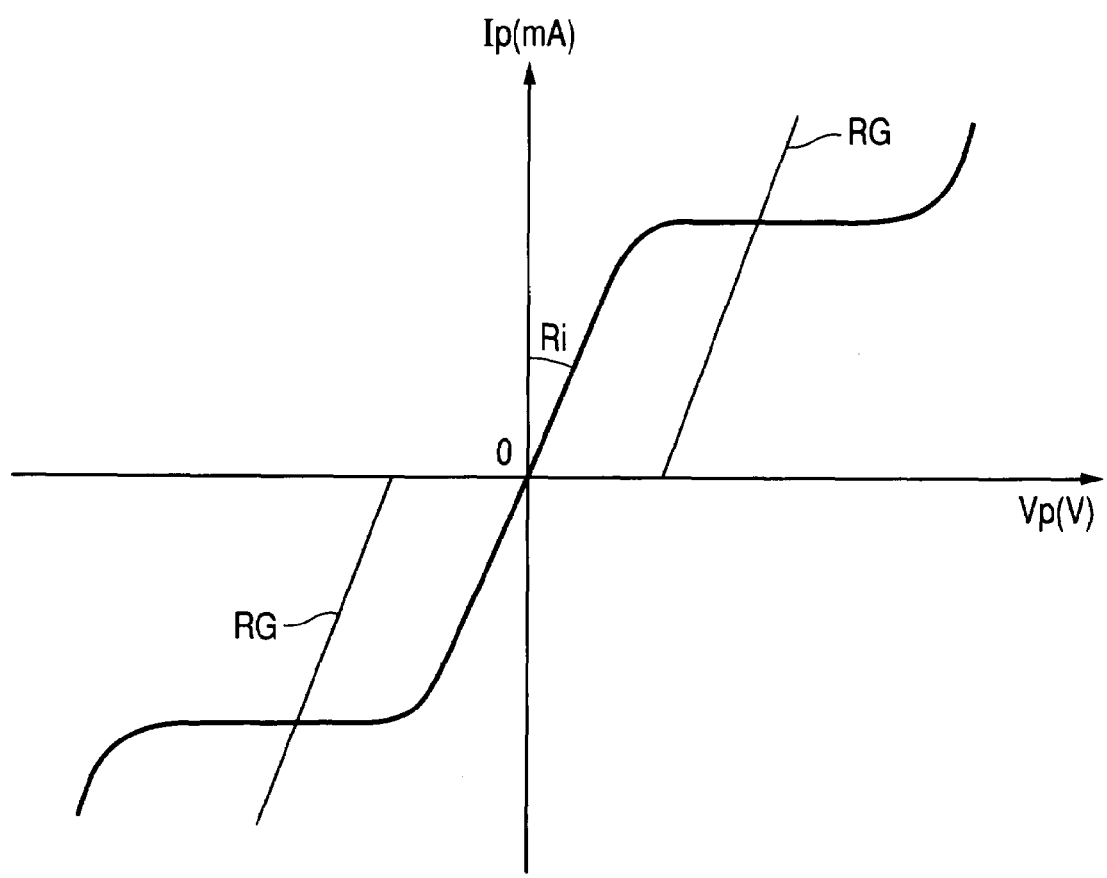
FIG. 15 shows an example of an applied voltage-to-output current map for use in determining a target voltage to be applied to the sensor element as illustrated in FIG. 14.

FIG. 15 shows a voltage-to-current relation (i.e., V-I characteristic) of the A/F sensor. Straight segments of a V-I curve extending parallel to the abscissa axis (i.e., Vp-axis) indicate limiting current ranges within which the sensor element 10 produces an electric current Ip (i.e., a limiting current) as a function of an air-fuel ratio (i.e., richness or leanness). Within a right one of the limiting current ranges lying in a positive voltage region, the electric current Ip is produced when the exhaust gasses are lean, while within the left limiting current range lying in a negative voltage region, the electric current Ip is produced when the exhaust gasses are rich.

Figure 16:
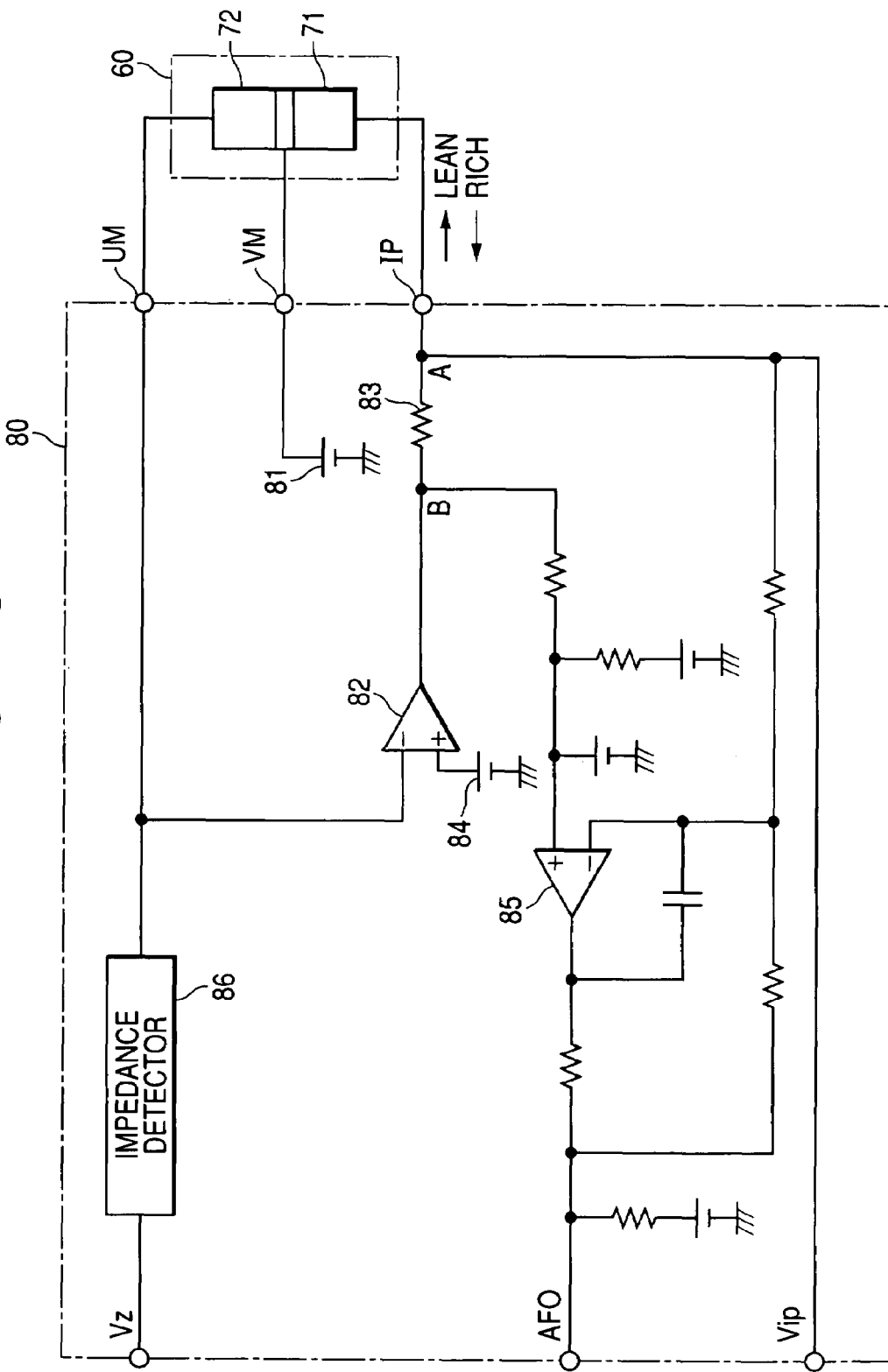
FIG. 16 is a circuit diagram which shows an internal structure of a sensor control circuit, as illustrated in FIG. 14.

The sensor control circuit 80 has a circuit structure, as illustrated in FIG. 16. A terminal VM is a common terminal shared between the pump cell 71 and the monitor cell 72. The common terminal VM is connected to a reference voltage source 81 which produces a reference voltage of, for example, 2.5V. The pump cell 71 is also connected at the electrode 63 to the terminal IP. The monitor cell 72 is also connected at the electrode 66 to the terminal UN. The terminals IP and UN form a closed circuit together with the cells 71 and 72, an operational amplifier 82, and a current-measuring resistor 83. The operational amplifier 82 is connected at a noninverting input (i.e., +terminal) thereof to a reference voltage source 84 which produces a reference voltage of 3.0V.

When the exhaust gases are lean, the current Ip flows through the current-measuring resistor 83 in the direction from the junction B to the junction A. Conversely, when the exhaust gasses are rich, the current Ip flows through the current-measuring resistor 83 in the direction from the junction A to the junction B. The sensor control circuit 80 also includes a feedback circuit (not shown) which works to control the voltage applied to the pump cell 71 to bring an output voltage of the monitor cell 72 into agreement with a target one. This feedback control is known in the art, and explanation thereof in detail will be omitted here.

The sensor control circuit 80 also includes an operational amplifier 85 and an impedance measuring circuit 86. The operational amplifier 85 is connected to the junctions A and B across the current-measuring resistor 83 and works to output the A/F output voltage AFO to the CPU 30 The voltage appearing at the IP terminal is outputted as a pump cell terminal voltage Vip to the CPU 30.

The impedance measuring circuit 86 works to sweep the voltage applied to the monitor cell 72 in an ac form and measure a resulting change in output voltage to output it as an impedance voltage Vz to the CPU 30.

The CPU 30 of this embodiment works to discriminate among the following twelve types of causes of failure of the A/F sensor.
(a) UN terminal disconnection
(b) VB short of UN terminal
(c) GND short of UN terminal
(d) UN-to-VM terminal short
(e) VM terminal disconnection
(f) VB short of VM terminal
(g) GND short of VM terminal
(h) VM-to-IP terminal short
(i) IP terminal disconnection
(j) VB short of IP terminal
(k) GND short of IP terminal
(l) IP-to-UN terminal short FIG. 17 is a table which demonstrates values of the impedance voltage Vz, the A/F output voltage AFO, and the pump cell terminal voltage Vip, as sampled when the A/F sensor is operating properly and in the events of the above twelve types (a) to (l) of causes of failure of the A/F sensor.

The first failure cause (a) is, like the first embodiment, disconnection of the UN terminal. The second failure cause (b) is an electrical short of the terminal UN to the battery installed in the vehicle. The third failure cause (c) is an electrical short of the terminal UN to ground. The fourth failure cause (d) is an electrical short between the terminals UN and VM. The same applies to the fifth to twelfth failure causes (e) to (l), and explanation thereof in detail will be omitted here. "○" in cells of the table represents a case where the A/F sensor is determined to be malfunctioning. "X" in cells represents a case where the A/F sensor is determined to be operating normally.

A normal value of each parameter listed in the table of FIG. 17 will first be described below.

Before the sensor element 60 is activated completely, it is infeasible to measure the sensor element impedance Zac, as represented by the impedance voltage Vz, correctly. Such measurement is, therefore, not made before the activation of the sensor element 60, so that the impedance voltage Vz shows zero (0) in the table. The A/F output voltage AFO is kept at a reference voltage of 2.5V. The pump cell terminal voltage Vip is kept at a constant voltage of 2.0V.

After the activation of the sensor element 60, the impedance voltage Vz converges at a value of, for example, 2.24V. The A/F output voltage AFO converges at a value corresponding to instantaneous exhaust gas atmosphere of the engine within a normal range of, for example, 1.6V to 4.1V. The pump cell terminal voltage Vip is controlled within a given range based on the current Ip flowing through the sensor element 60.

Next, values of the impedance voltage Vip, the A/F output voltage AFO, and the pump cell terminal voltage Vip in the events of the above types of causes (a) to (h) of failure of the A/F sensor will be described below.

If the first type of cause (a) of failure has occurred, that is, if disconnection has occurred at the terminal UN, the impedance voltage Vz and the A/F output voltage AFO are also kept at zero (0) after the activation of the sensor element 60.

If any of the second to fourth types of causes (b) to (d) of failure (i.e., the VB short of the terminal UN, the GND short of the terminal UN, and the UN-to-VM terminal short) has occurred, the impedance voltage Vz is fixed at 5.0V that is an upper limit of an output voltage range of the sensor control circuit 80. However, in the event of the VB short of the terminal UN, the pump cell terminal voltage Vip is fixed at 0V before and after the activation of the sensor element 60. In the event of the GND short of the terminal UN, the pump cell terminal voltage Vip is fixed at 5V before and after the activation of the sensor element 60. In the event of the UN-to-VM terminal short, the pump cell terminal voltage Vip has an unusual value of 2.5V.

If either of the sixth and seventh types of causes (f) and (g) of failure (i.e., the VB short of the terminal VM and the GND short of the terminal VM) has occurred, the pump cell terminal voltage Vip is fixed at 5.0V after the activation of the sensor element 60. However, in the event of the VB short of the terminal VM, the A/F output voltage AFO is fixed at 0V after the activation of the senor element 60. In the event of the GND short of the terminal VM, the A/F output voltage AFO is fixed at 5.0V after the activation of the sensor element 60.

If the eighth type of cause (h) of failure (i.e., the VM-to-LP terminal short) has occurred, the pump cell terminal voltage Vip is fixed at a reference voltage of 2.5V before the activation of the sensor element 60. The A/F output voltage AFO is fixed at 5.0V after the activation of the sensor element 60.

If the ninth type of cause (i) of failure (i.e., the IP terminal disconnection) has occurred, the pump cell terminal voltage Vip is fixed at 5.0V that is the upper limit of the output voltage range of the sensor control circuit 80.

If the tenth type of cause (j) of failure (i.e., the VB short of the IP terminal) has occurred, the pump cell terminal voltage Vip is fixed at 5.0V before and after the activation of the sensor element 60. The A/F output voltage AFO is fixed at 0V before and after the activation of the sensor element 60.

If the eleventh type of cause (k) of failure (i.e., the GND short of the terminal IP) has occurred, the pump cell terminal voltage Vip is fixed at 0V that is a lower limit of the output voltage range of the sensor control circuit 80 before and after the activation of the sensor element 60. The A/F output voltage AFO is fixed at 5.0V before and after the activation of the sensor element 60.

If the twelfth type of cause (l) of failure (i.e., the IP-to-UN terminal short) has occurred, the pump cell terminal voltage Vip is held at 3.0V before the activation of the sensor element 60 that is the reference voltage of the operational amplifier 82 working as a pump cell voltage controller.

Figure 18:
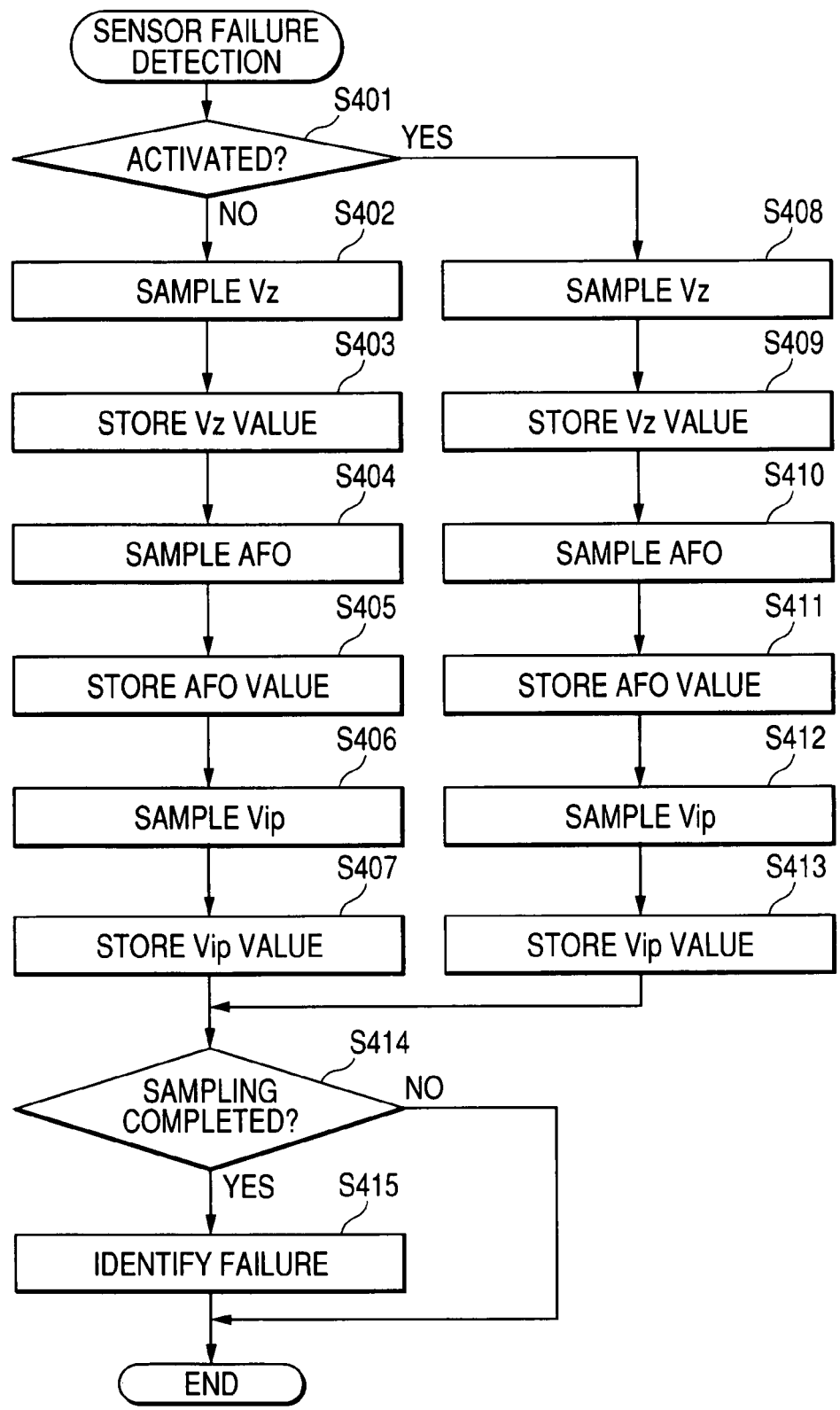
FIG. 18 is a flowchart of a program to be executed to detect and identify the cause of failure in an A/F sensor using the table of FIG. 17.

FIG. 18 is a flowchart of a program to be executed by the CPU 30 to discriminate among the first to twelfth types of causes (a) to (l) of failure of the A/F sensor. The program is performed instead of the ones as illustrated in FIGS. 7 and 9.

After entering the program, the routine proceeds to step 401 wherein it is determined that the sensor element 60 has been activated completely or not. If a NO answer is obtained, then the routine proceeds to step 402 wherein the value of the impedance voltage Vz is sampled. The routine proceeds to step 403 wherein the value of the impedance voltage Vz, as sampled in step 402, is compared with a normal one, and a result of the comparison is stored in the memory built in the CPU 30.

The routine proceeds to step 404 wherein the value of the A/F output voltage AFO is sampled. The routine proceeds to step 405 wherein the value of the A/F output voltage AFO, as sampled in step 404, is compared with a normal one, and a result of the comparison is stored in the memory.

The routine proceeds to step 406 wherein the value of the pump cell terminal voltage Vip is sampled. The routine proceeds to step 407 wherein the value of the pump cell terminal voltage Vip, as sampled in step 406, is compared with a normal one, and a result of the comparison is stored in the memory.

If a YES answer is obtained in step 401 meaning that the sensor element 60 has been activated completely, then the routine proceeds to step 408 wherein the value of the impedance voltage Vz is sampled. The routine proceeds to step 409 wherein the value of the impedance voltage Vz, as sampled in step 408, is compared with a normal one, and a result of the comparison is stored in the memory built in the CPU 30.

The routine proceeds to step 410 wherein the value of the A/F output voltage AFO is sampled. The routine proceeds to step 411 wherein the value of the A/F output voltage AFO, as sampled in step 410, is compared with a normal one, and a result of the comparison is stored in the memory.

The routine proceeds to step 412 wherein the value of the pump cell terminal voltage Vip is sampled. The routine proceeds to step 413 wherein the value of the pump cell terminal voltage Vip, as sampled in step 412, is compared with a normal one, and a result of the comparison is stored in the memory.

After step 407 or 413, the routine proceeds to step 414 wherein all data, as required to identify the cause of failure of the A/F sensor, have been sampled or not. If a YES answer is obtained, then the routine proceeds to step 415 wherein the values of the impedance voltage Vz, the A/F output voltage AFO, and the pump cell terminal voltage Vip are read out of the memory to identify the cause of failure of the A/F sensor. Specifically, a combination of the values of impedance voltage Vz, the A/F output voltage AFO, and the pump cell terminal voltage Vip is looked up from the table of FIG. 18 to discriminate among the causes (a) to (l) of failure of the A/F sensor in a similar manner, as described in the first and second embodiments.

The CPU 30 of the fifth embodiment works to analyze only three failure-detecting parameters: the values of the impedance voltage Vz, the A/F output voltage AFO, and the pump cell terminal voltage Vip inputted to A/D ports of the CPU 30 and may, thus, designed to have a simplified structure.

The CPU 30 may also be designed to additionally monitor voltages appearing at the UN terminal and the VM terminal in order to increase the types of failures of the A/F sensor to be identified.

Figure 19:
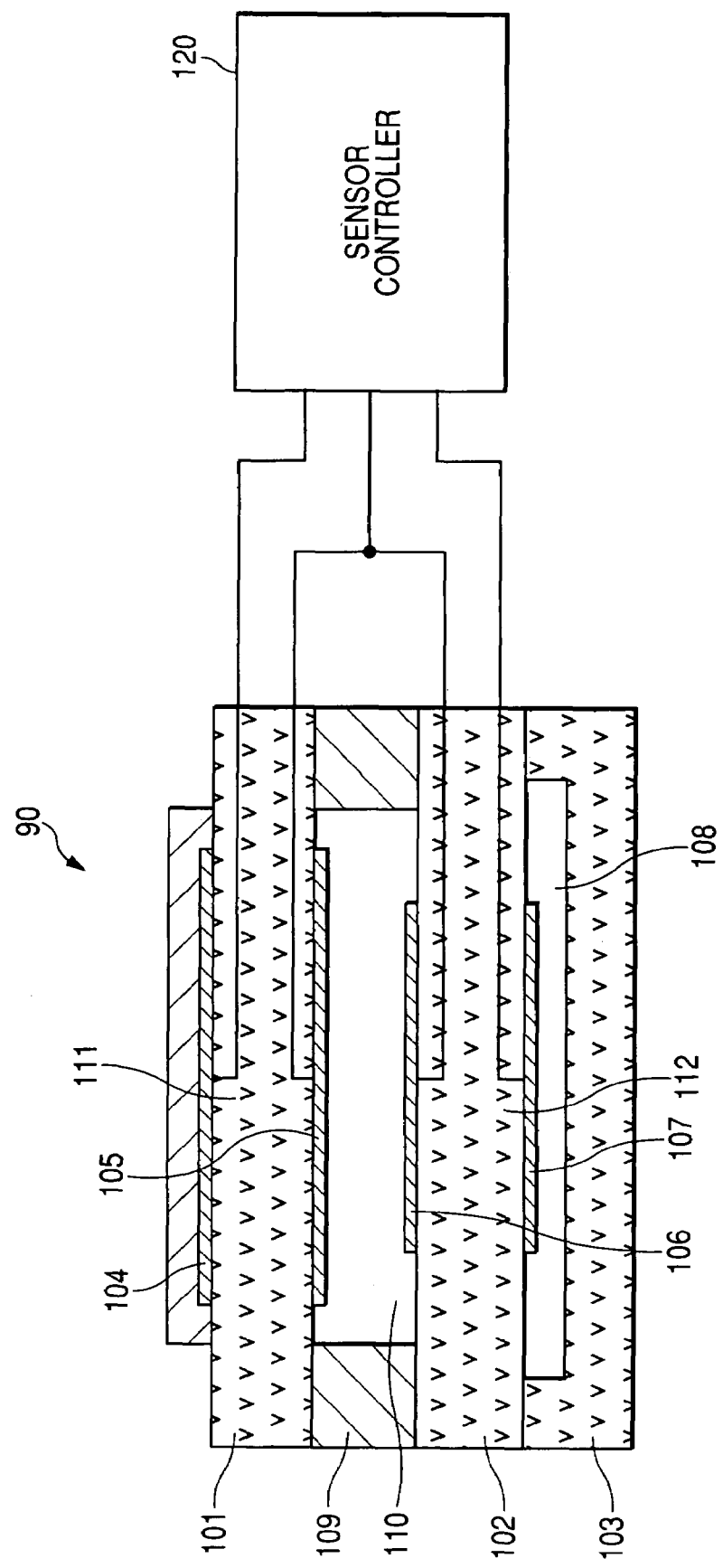
FIG. 19 is a transverse sectional view which shows a sensor element of a gas concentration measuring apparatus according to the fifth embodiment of the invention.

FIG. 19 shows a sensor element 90 which may be built in the A/F sensor, as employed in each of the above embodiments.

The sensor element 90 includes three solid electrolyte layers 101, 102, and 103. The solid electrolyte layer 101 has electrodes 104 and 105 affixed to opposed surfaces thereof. Similarly, the solid electrolyte layer 102 has electrodes 106 and 107 affixed to opposed surfaces thereof. The solid electrolyte layer 101 and the electrodes 104 and 105 form a pump cell 111. The solid electrolyte layer 102 and the electrodes 106 and 107 form a monitor cell 112. The solid electrolyte layer 103 forms a wall defining an oxygen reference chamber 108. The sensor element 90 is, like the sensor element 10, of a laminated structure. The sensor element 90 also includes a porous diffusion layer 109 and a gas chamber 110 into which exhaust gasses of the automotive engine enter. The monitor cell 112 operates, like the monitor cell 72 illustrated in FIG. 14, as an electromotive force cell or an oxygen concentration sensor cell.

The CPU 30 of the sixth embodiment will be described blow which is a modification of the one in the first embodiment. The CPU 30 of this embodiment is designed to detect the T1-to-T2 terminal short using the voltages VS+ and VS− appearing at the terminals T1 and T2 and the A/F output voltage AFO.

Figure 20:
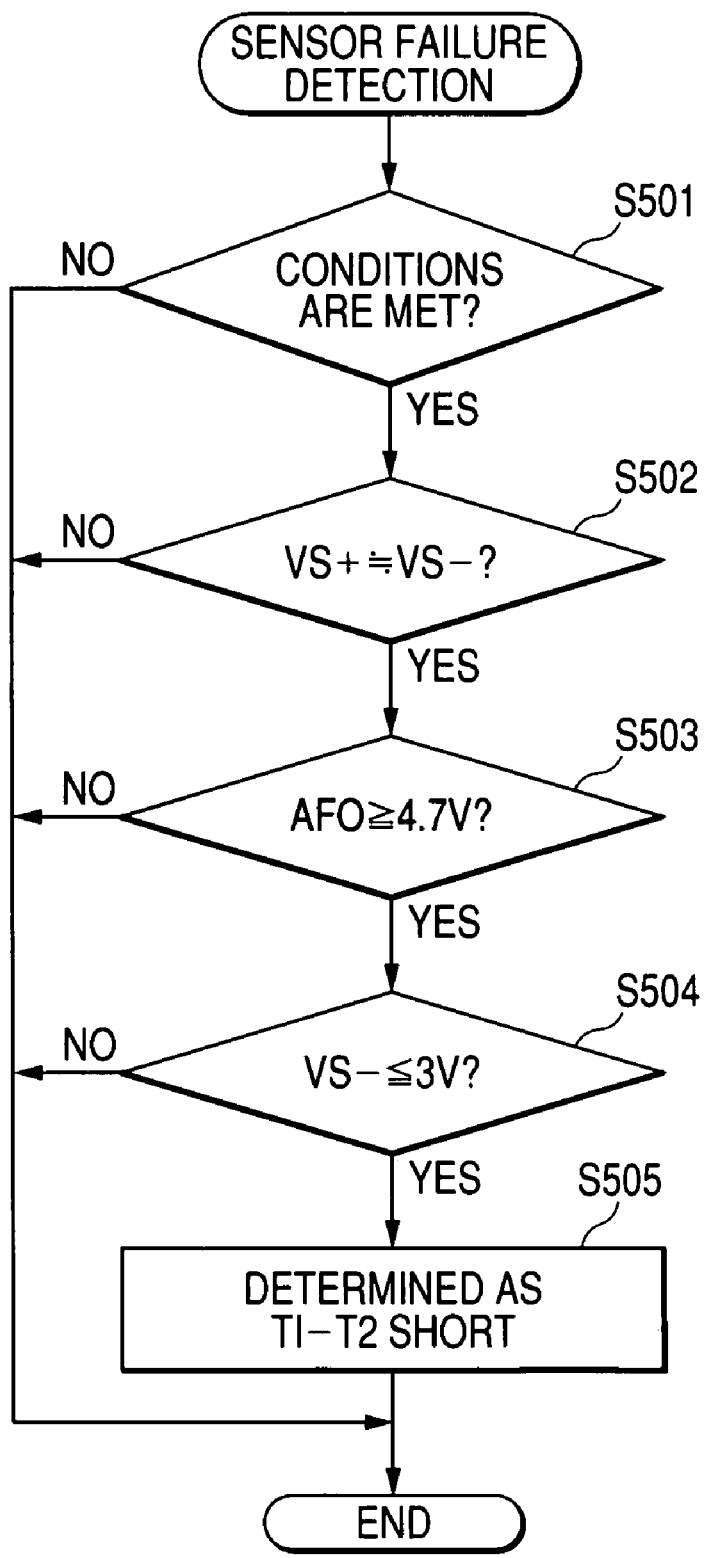
FIG. 20 is a flowchart to be executed to detect and identify the cause of failure in an A/F sensor of a gas concentration measuring apparatus according to the sixth embodiment of the invention.

FIG. 20 is a flowchart of a failure monitoring program to be executed by the CPU 30 of the sixth embodiment.

First, in step 501, it is determined whether failure monitoring enable conditions are met or not. For example, it is determined whether the battery voltage lies within a normal range of 11 to 16V or not, the voltage of a power supply for the heater 18, as illustrated in FIG. 2, is at 11V or not, an operating voltage for the CPU 30 is at a given constant level or not, and a ground potential is normal or not. If these conditions are all encountered, then the routine proceeds to step 502 wherein it is determined whether the voltage VS+ appearing at the terminal T1 is substantially identical with the voltage VS− appearing at the terminal T2 or not. For example, it is determined whether a difference between the voltages VS+ and VS− is smaller than a given level (e.g., 0.1V) or not. If a YES answer is obtained, then the routine proceeds to step 503 wherein the A/F output voltage AFO shows an unusual value or not, for example, whether it is smaller than 4.7V or not.

If a YES answer is obtained in step 503, then the routine proceeds to step 504 wherein it is determined whether the voltage VS− appearing at the terminal T2 shows an unusual value or not, for example, whether it is lower than 3V or not. 3V is a threshold value for determining whether the voltage VS− lies within the applied-voltage control range of the voltage application control circuit 25 or not. The threshold value may be selected with a certain margin between the applied-voltage control range (e.g., 1.1 to 2.2V) and a value (e.g., 5.0V) of the voltage VS− when the terminal T1 or T2 is short-circuited to the battery. In step 104, the voltage VS+ appearing at the terminal T1 may be used instead of the voltage VS−. Not that the parameter used in each of steps 501 to 504 may be what is sampled either before or after the activation of the sensor element 10.

If a YES answer is obtained in step 504 meaning that the voltage VS− lies within the applied-voltage control range of the voltage application control circuit 25, then the routine proceeds to step 505 wherein it is determined that an electrical short has occurred between the terminals T1 and T2. Alternatively, when a flow of step 510 to 505 has been consecutively repeated several times, it may ultimately be determined in step 505 that the terminals T1 and T2 are short-circuited. In the event of the T1-to-T2 terminal short, a warning is turned on. Diagnosis information is stored in a backup RAM in the CPU 30. The heater 18 of the sensor element 10 is turned off. Upon subsequent turning on of the ECU 20, the failure monitoring program will be executed again.

The program of FIG. 20 may alternatively be executed in the structure of FIG. 12 using the table of FIG. 13.

Specifically, if three conditions are met: (1) the voltages VS+ and VS− appearing at the terminals T1 and T2 are identical with each other, (2) the voltage VS+ or VS− lies within the applied-voltage control range of the voltage application control circuit 45, and (3) the A/F output voltage AFO has an unusual value, it is determined that the T1-to-T2 terminal short has occurred.

The determination that the T1-to-T2 terminal short has occurred may alternatively be made when two conditions are encountered: (1) the voltages VS+ and VS− appearing at the terminals T1 and T2 before the activation of the sensor element 10 are identical with each other, and (2) the A/F output voltage AFO before the activation of the sensor element 10 has an unusual value. Specifically, FIGS. 5 and 8 show that when the terminals T1 and T2 are short-circuited, it will cause the A/F output voltage AFO to show an unusual value and the voltages VS+ and VS− to have the same value before the activation of the sensor element 10. This is a parameter pattern different from that in the event of another failure of the A/F sensor and thus may be used for detecting the T1-to-T2 terminal short.

The A/F sensor, as employed in each of the above embodiments, may also be designed to have two- or three-cell structure. The sensor element 10, 60, or 90 may be of a cup-shaped type known in the art. The A/F sensor may also be implemented by a typical $O_2$ sensor designed to produce an electromotive force between electrodes affixed to a sensor element as a function of concentration of oxygen contained in exhaust emissions of an automotive engine.

The gas concentration measuring apparatus, as described in each of the above embodiments, may be used with a composite gas concentration measuring sensor which includes first and second cells made of a solid electrolyte body. The first cell works as a pump cell to pump oxygen molecules out of or into a first gas chamber formed in a sensor body and output a signal indicative of the concentration of the pumped oxygen molecules. The second cell works as a sensor cell to produce a signal indicative of the concentration of a preselected component of gasses flowing into a second gas chamber from the first gas chamber. For example, the composite gas concentration measuring sensor may be used to measure the concentration NOx contained in exhaust gasses of the automotive engine. Further, the composite gas concentration measuring sensor may be designed to have a third cell serving as a monitor cell or a second pump cell to produce an electromotive force as a function of concentration of oxygen molecules remaining in the second gas chamber. The sensor element impedance Zac may be given by the impedance of any one of the pump, sensor, and monitor cell.

The gas concentration measuring sensor may alternatively be designed to measure the concentration of HC or CO contained in the exhaust gasses of the automotive engine. The measurement of concentration of HC or CO is achieved by pumping excessive oxygen ($O_2$) out of the first gas chamber using the pump cell and decomposing HC or CO contained in the gasses entering the second gas chamber using the sensor cell to produce an electric signal indicative of the concentration of HC or CO.

The gas concentration measuring apparatus in each of the above embodiment may alternatively be employed to measure the concentration of a gas other than a preselected component contained in exhaust emissions of automotive engines.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas concentration measuring apparatus comprising:
a gas concentration sensor equipped with a sensor element which is made of a solid electrolyte body and a pair of electrodes affixed to the solid electrolyte body;
a sensor control circuit connected to the electrodes of the sensor element through a positive and a negative terminal, when a gas concentration measuring mode is entered, said sensor control circuit applying a voltage across the electrodes of the sensor element to produce a flow of electrical current through the sensor element and sampling the electrical current through a current-measuring resistor to output a sensor current signal as indicating a concentration of a gas to be measured, when an internal resistance measuring mode is entered, said sensor control circuit working to perform one of a voltage sweep mode and a current sweep mode, in the voltage sweep mode, said sensor control circuit applying a voltage to the sensor element and sweeping the applied voltage in an ac form to sample a resulting change in voltage provided by the sensor element, in the current sweep mode, said sensor control circuit supplying a current to the sensor element and sweeping the supplied current in an ac form to sample a resulting change in current provided by the sensor element, said sensor control circuit outputting one of the resulting changes in voltage and current as an internal resistance signal; and
a failure monitor working to sample values of the sensor current signal before and after the sensor element is activated and a value of the internal resistance signal after the sensor element is activated, said failure monitor detecting a failure in said gas concentration sensor based on the sampled values.

2. A gas concentration measuring apparatus as set forth in claim 1, wherein said failure monitor determines whether said gas concentration sensor is failing or not based on the value of the internal resistance signal, as sampled after said gas concentration sensor is activated, and also identifies a cause of failure of said gas concentration sensor based on the values of the sensor current signals, as sampled before and after said gas concentration sensor is activated.

3. A gas concentration measuring apparatus as set forth in claim 1, wherein the current-measuring resistor is connected to one of the positive and negative terminals, and wherein when the gas concentration measuring mode is entered, said failure monitor samples, instead of the value of the sensor current signal, a voltage appearing at an end of the current-measuring resistor which changes as a function of the current flowing through the sensor element, when the internal resistance measuring mode is entered, said failure monitor sampling, as the value of the internal resistance signal, a voltage appearing at the end of the current-measuring resistor which changes as a function of an internal resistance of the sensor element.

4. A gas concentration measuring apparatus as set forth in claim 1, wherein said failure monitor also samples at least one of voltages appearing at the positive and negative terminals one of before and after the sensor element is activated, said failure monitor detecting the failure of said gas concentration sensor based on the sampled one of the voltages in addition to the values of the sensor current signal, as sampled before and after the sensor element is activated and the value of the internal resistance signal, as sampled after the sensor element is activated.

5. A gas concentration measuring apparatus as set forth in claim 4, wherein said failure monitor monitors whether the sampled one of the voltages developed at the positive and negative terminals is held at an upper or a lower limit of an input signal voltage range of said sensor control circuit to identify whether said gas concentration sensor is short-circuited to a power supply or ground.

6. A gas concentration measuring apparatus as set forth in claim 1, said failure monitor stores therein a table listing unusual values shown by the sensor current signal and the internal resistance signal when said gas concentration sensor is failing in operation and looks up a combination of the sampled values from the table to identify a cause of the failure of said gas concentration sensor.

7. A gas concentration measuring apparatus as set forth in claim 1, wherein said failure monitor samples the values of the sensor current signal and the internal resistance signal at times other than during transition of activation of the sensor element.

8. A gas concentration measuring apparatus comprising:
a gas concentration sensor equipped with a sensor element which is made of a solid electrolyte body and a pair of electrodes affixed to the solid electrolyte body;
a sensor control circuit connected to the electrodes of the sensor element through a positive and a negative terminal, when a gas concentration measuring mode is entered, said sensor control circuit applying a voltage across the electrodes of the sensor element to produce a flow of electrical current through the sensor element and sampling the electrical current through a current-measuring resistor connected to one of the positive and negative terminals to output a sensor current signal as indicating a concentration of a gas to be measured, when an internal resistance measuring mode is entered, said sensor control circuit working to perform one of a voltage sweep mode and a current sweep mode, in the voltage sweep mode, said sensor control circuit applying a voltage to the sensor element and sweeping the applied voltage in an ac form to sample a resulting change in voltage provided by the sensor element, in the current sweep mode, said sensor control circuit supplying a current to the sensor element and sweeping the supplied current in an ac form to sample a resulting change in current provided by the sensor element, said sensor control circuit outputting one of the resulting changes in voltage and current as an internal resistance signal; and a failure monitor working to sample values of voltages appearing at the other of the positive and negative terminals before and after the sensor element is activated and a value of the internal resistance signal after the sensor element is activated, said failure monitor detecting a failure in said gas concentration sensor based on the sampled values.

9. A gas concentration measuring apparatus as set forth in claim 8, wherein said failure monitor determines whether said gas concentration sensor is failing or not based on the value of the internal resistance signal, as sampled after said gas concentration sensor is activated and also identifies a cause of failure of said gas concentration sensor based on the values of the voltages, as sampled before and after said gas concentration sensor is activated.

10. A gas concentration measuring apparatus as set forth in claim 8, said failure monitor stores therein a table listing unusual values shown by the internal resistance signal and the voltages when said gas concentration sensor is failing in operation and looks up a combination of the sampled values from the table to identify a cause of the failure of said gas concentration sensor.

11. A gas concentration measuring apparatus as set forth in claim 8, wherein said failure monitor samples the values of the internal resistance signal and the voltages at times other than during transition of activation of the sensor element.

12. A gas concentration measuring apparatus comprising:
a gas concentration sensor equipped with a sensor element which includes a first cell and a second cell, the first cell being made of a solid electrolyte material and working to perform an oxygen pumping operation to produce an electrical current as a function of a pumped amount of oxygen, the second cell being made of a solid electrolyte material and working to produce an electromotive force as a function of a concentration of oxygen contained in a gas to be measured;
a sensor control circuit working to perform a gas concentration measuring mode and an internal resistance measuring mode, when the gas concentration measuring mode is entered, said sensor control circuit applying a voltage to the first cell, controlling the applied voltage as a function of the electromotive force produced by the second cell to produce a flow of an electrical current through the first cell, and sampling the electrical current through a current-measuring resistor to output the sampled electrical current as a sensor current signal as indicating a concentration of a gas to be measured, when the internal resistance measuring mode is entered, said sensor control circuit working to perform one of a voltage sweep mode and a current sweep mode, in the voltage sweep mode, said sensor control circuit applying a voltage to the second cell and sweeping the applied voltage in an ac form to sample a resulting change in voltage provided by the second cell, in the current sweep mode, said sensor control circuit supplying a current to the second cell and sweeping the supplied current in an ac form to sample a resulting change in current provided by the second cell, said sensor control circuit outputting one of the resulting changes in voltage and current as an internal resistance signal; and
a failure monitor working to sample values of the sensor current signal, the internal resistance signal, and voltages appearing at at least one of positive and negative terminals connected to the first cell before and after the sensor element is activated, said failure monitor detecting a failure in said gas concentration sensor based on the sampled values.

13. A gas concentration measuring apparatus as set forth in claim 12, wherein said failure monitor works to discriminate among a disconnection, a short to a power supply, a short to ground, and a terminal-to-terminal short of each of the positive and negative terminals connected to the first cell and positive and negative terminal connected to the second cell.

14. A gas concentration measuring apparatus as set forth in claim 12, wherein the second cell is connected to a positive and a negative terminal one of which is a common terminal shared with one of the positive and negative terminals connected to the first cell, the common terminal being applied with a reference voltage, and wherein said failure monitor samples voltages appearing at one of the positive and negative terminals connected to the first cell that is not the common terminal before and after the sensor element is activated.

15. A gas concentration measuring apparatus as set forth in claim 12, said failure monitor stores therein a table listing unusual values shown by the internal resistance signal, the sensor current signal, the internal resistance signal, and the voltages appearing at the one of the positive and negative terminals connected to the first cell when said gas concentration sensor is failing in operation, said failure monitor looking up a combination of the sampled values from the table to identify a cause of the failure of said gas concentration sensor.

16. A gas concentration measuring apparatus as set forth in claim 12, wherein said failure monitor samples the values of the sensor current signal, the internal resistance signal, and the voltages appearing at the one of the positive and negative terminals connected to the first cell at times other than during transition of activation of the sensor element before and after the sensor element is activated.

17. A gas concentration measuring apparatus comprising:
a gas concentration sensor equipped with a sensor element which is made of a solid electrolyte body and a pair of electrodes affixed to the solid electrolyte body;
a sensor control circuit connected to the electrodes of the sensor element through a positive and a negative terminal, when a gas concentration measuring mode is entered, said sensor control circuit applying a voltage across the electrodes of the sensor element within a given applied-voltage control range to produce a flow of electrical current through the sensor element and sampling the electrical current to output a sensor current signal as indicating a concentration of a gas to be measured, said sensor control circuit also sampling voltages appearing at the positive and negative terminals; and
a failure monitor working to monitor a failure in said gas concentration sensor, when the voltages at the positive and negative terminals, as sampled by said sensor control circuit, are identical with each other, one of the voltages at the positive and negative terminals lies within the applied-voltage control range, and the sensor current signal has an unusual value, said failure monitor determining that an electrical short has occurred between the positive and negative terminals.

18. A gas concentration measuring apparatus as set forth in claim 17, wherein when the one of the voltages at the positive and negative terminals is less than a given threshold level, said failure monitor determines that the one of the voltages lies within the applied-voltage control range.

19. A gas concentration measuring apparatus comprising:

a gas concentration sensor equipped with a sensor element which is made of a solid electrolyte body and a pair of electrodes affixed to the solid electrolyte body;

a sensor control circuit connected to the electrodes of the sensor element through a positive and a negative terminal, when a gas concentration measuring mode is entered, said sensor control circuit applying a voltage across the electrodes of the sensor element within a given applied-voltage control range to produce a flow of electrical current through the sensor element and sampling the electrical current to output a sensor current signal as indicating a concentration of a gas to be measured, said sensor control circuit also sampling voltages appearing at the positive and negative terminals; and a failure monitor working to monitor a failure in said gas concentration sensor, when the voltages at the positive and negative terminals, as sampled by said sensor control circuit before said sensor element is activated, are identical with each other, and the sensor current signal has an unusual value, said failure monitor determining that an electrical short has occurred between the positive and negative terminals.

* * * * *